US006782307B2

(12) United States Patent
Wilmott et al.

(10) Patent No.: US 6,782,307 B2
(45) Date of Patent: Aug. 24, 2004

(54) METHOD FOR PRODUCING CUSTOMIZED COSMETIC AND PHARMACEUTICAL FORMULATIONS ON DEMAND

(75) Inventors: James M. Wilmott, Shoreham, NY (US); Duncan T. Aust, Carson City, NV (US); Timothy K. Crawford, Manchester, IA (US)

(73) Assignee: Lab21, Inc., New York, NY (US)

( * ) Notice: Subject to any disclaimer, the term of this patent is extended or adjusted under 35 U.S.C. 154(b) by 0 days.

(21) Appl. No.: 09/972,848

(22) Filed: Oct. 1, 2001

(65) Prior Publication Data

US 2002/0082745 A1 Jun. 27, 2002

Related U.S. Application Data

(63) Continuation of application No. PCT/US01/03168, filed on Jan. 31, 2001.
(60) Provisional application No. 60/216,847, filed on Jul. 7, 2000, provisional application No. 60/191,878, filed on Mar. 23, 2000, and provisional application No. 60/179,057, filed on Jan. 31, 2000.

(51) Int. Cl.[7] ............................................. G06F 17/00
(52) U.S. Cl. ..................... 700/233; 700/236; 700/239
(58) Field of Search ............................... 700/216, 231, 700/232, 233, 234, 239, 236, 240; 222/52, 144; 424/401

(56) References Cited

U.S. PATENT DOCUMENTS

| | | | |
|---|---|---|---|
| 4,107,288 A | 8/1978 | Oppenheim et al. | 424/22 |
| 4,540,602 A | 9/1985 | Motoyama et al. | 427/213 |
| 4,753,788 A | 6/1988 | Gamble | 424/1.1 |
| 4,871,262 A | 10/1989 | Krauss et al. | 366/160 |
| 4,927,637 A | 5/1990 | Morano et al. | 424/450 |
| 5,039,527 A | 8/1991 | Tabibi et al. | 424/450 |
| 5,115,874 A | 5/1992 | Hayahara et al. | 177/70 |
| 5,118,528 A | 6/1992 | Fessi et al. | 427/213 |
| 5,145,684 A | 9/1992 | Liversidge et al. | 424/489 |
| 5,163,010 A | 11/1992 | Klein et al. | 364/479 |
| 5,228,905 A | 7/1993 | Grunewalder et al. | 106/2 |
| 5,342,609 A | 8/1994 | Meeh et al. | 424/9 |
| 5,399,363 A | 3/1995 | Liversidge et al. | 424/490 |
| 5,520,203 A | 5/1996 | Segerstrom | 132/297 |
| 5,622,692 A | 4/1997 | Rigg et al. | 424/63 |
| 5,643,341 A | 7/1997 | Hirsch et al. | 8/405 |
| 5,643,555 A | 7/1997 | Collin et al. | 424/59 |
| 5,667,789 A | 9/1997 | Collin et al. | 424/401 |
| 5,785,960 A | 7/1998 | Rigg et al. | 424/63 |
| 5,833,951 A | 11/1998 | Artz et al. | 424/47 |
| 5,857,589 A | 1/1999 | Cline et al. | 222/1 |
| 5,903,465 A | 5/1999 | Brown | 364/479.12 |
| 5,945,112 A | 8/1999 | Flynn et al. | 424/401 |
| 5,950,630 A | * 9/1999 | Portwood et al. | 128/897 |

(List continued on next page.)

FOREIGN PATENT DOCUMENTS

DE 19704693 2/1997 ............ A61K/7/48

*Primary Examiner*—Khoi H. Tran
(74) *Attorney, Agent, or Firm*—Darby & Darby

(57) ABSTRACT

A method and system for selecting and producing a customized cosmetic or pharmaceutical formulation is disclosed below. The system can be implemented in an Internet based system or a stand-alone version, such as a Kiosk. An improved method of custom formulation is presented which utilizes the user's preferences and profile, as well as external factors. The customized formulation can be directed to a manufacturing facility for on-demand production. Alternatively, a printout of the formulation can be provided for subsequent use at point-of-sale locations, such as a cosmetics store or a pharmacy. The custom formulation software can also be provided in conjunction with a cosmetics manufacturing kit for use in home or business application.

7 Claims, 24 Drawing Sheets

U.S. PATENT DOCUMENTS

| | | |
|---|---|---|
| 5,992,686 A | 11/1999 | Cline et al. .................... 222/1 |
| 5,993,792 A | 11/1999 | Rath et al. ............... 424/70.28 |
| 6,000,837 A | 12/1999 | Randsborg et al. ......... 366/141 |
| 6,013,270 A | 1/2000 | Hargraves et al. .......... 424/401 |
| 6,123,934 A | 9/2000 | Koyama et al. ............. 424/70 |
| 6,136,328 A | 10/2000 | Sebillotte-Arnaud et al. .............. 424/401 |
| 6,177,093 B1 * | 1/2001 | Lombardi et al. .......... 424/401 |
| 6,228,377 B1 | 5/2001 | Sebillotte-Arnaud ........ 424/401 |
| 6,264,965 B1 | 7/2001 | Roulier et al. .............. 424/401 |
| 6,330,491 B1 * | 12/2001 | Lion .......................... 700/237 |
| 6,437,866 B1 * | 8/2002 | Flynn ......................... 356/402 |
| 6,510,366 B1 * | 1/2003 | Murray et al. .............. 700/239 |
| 6,516,245 B1 * | 2/2003 | Dirksing et al. ............ 700/233 |

\* cited by examiner

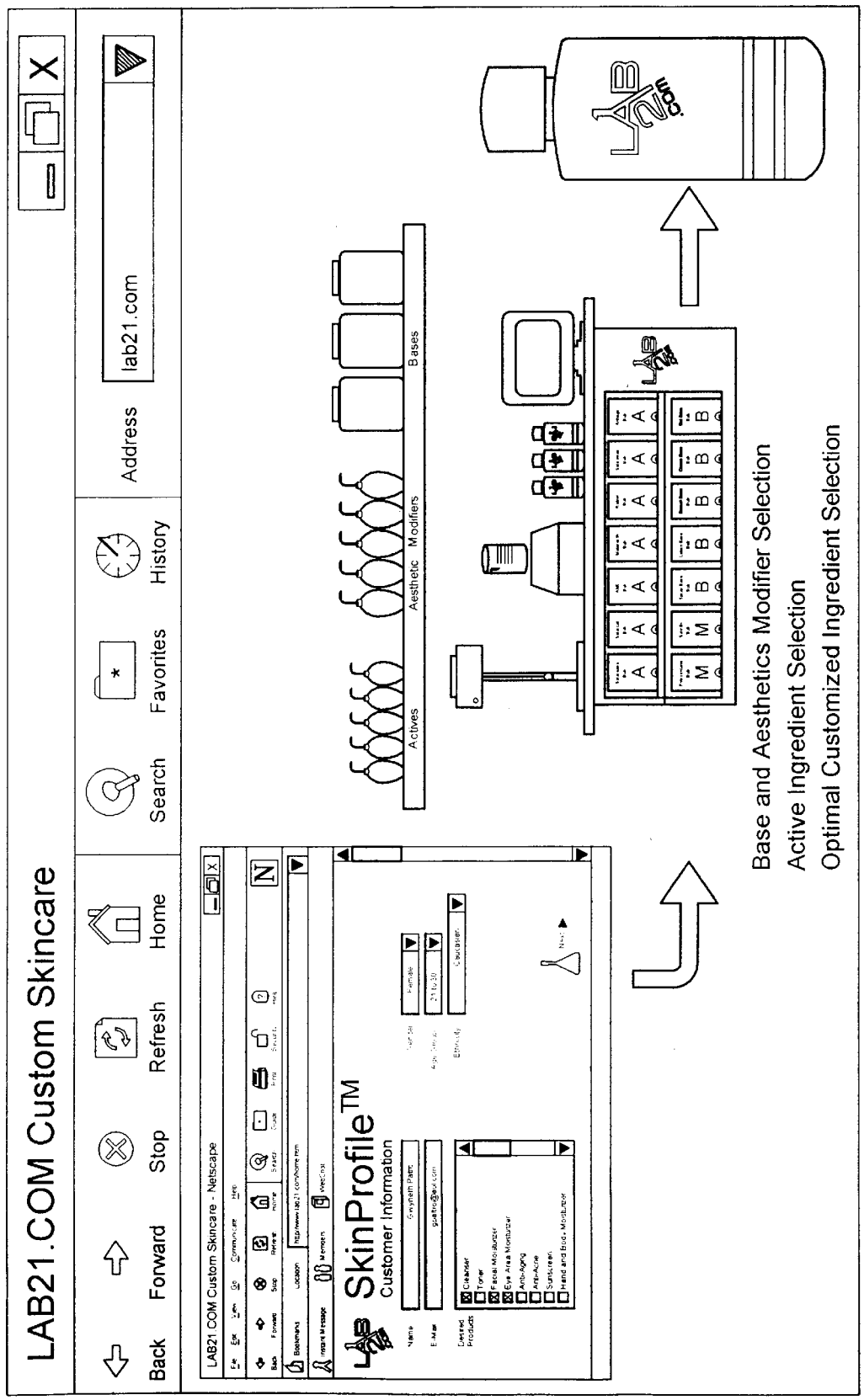
FIG. X1

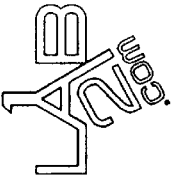
FIG. X2

FIG. X3-A

General Information

① Name
Jennifer Anniston

② e-mail
JAnniston@aol.com

③ Products Desired
- Soap
- Cleanser
- Facial Scrub/ • Exfoliator
- Toner
- Astringent
- Facial Moisturizer
- Eye Area Moisturizer
- Anti-Aging
- Anti-Acne
- Anti-Bacterial

- Lip
- Mask
- Sunscreen
- Self-Tanner
- Skin Lightener
- Hand Moisturizer
- Body Moisturizer
- Let us make some suggestions ④ Gender
Male or Female ⑤ Age Group
- Under 12
- 12 to 15
- 16 to 20
- 21 to 30
- 30 to 40
- 40 to 50
- 50 to 60
- 60 to 70
- 70 to 80
- Over 80

⑥ Ethnicity
- American-Indian
- Asian
- Black
- Caucasian
- Hispanic
- Other ⑦ Climate
Please click on the line below in the position that best describes the climate where you will be using your skin care products:

Dry ——————————▯—————— Humid

⑦ Prescription Skincare
Are you currently using any prescription skincare products prescribed by a physician?
Yes or No

FIG. X3-B

⑨ Natural Skin Coloring
Please click on the line below in the position that best describes your natural skin coloring:

very light ——————☐—————— very dark

⑩ Response to the Sun
Please click on the line below in the position that best describes the response of your skin when exposed to the sun:

always burns ——————☐—————— always tans

⑪ Sensitivity
Please click on the line below in the position that best describes your skin sensitivity:

very sensitive ——————☐—————— not sensitive

⑫ Pore Size
Please click on the line below in the position that best describes your pore size:

invisible ——————☐—————— large

⑬ Breakout
Please click on the line below in the position that best describes how often your skin tends to breakout:

never ——————☐—————— daily

⑭ Your Skin's Average Day
Please click on the line below in the position that best describes how your skin feels on an average day in the middle of the afternoon:

| very oily | | very dry |
|---|---|---|
| Forehead | ☐ | |
| Nose | ☐ | |
| Cheeks | | ☐ |
| Chin | | ☐ |
| Body | ☐ | |
| Arms / Legs | | ☐ |

*Skin Type*

FIG. X3-C

15 Sun Exposure

Please click on the line below in the position that best describes how much time you spend in the sun daily:

a few minutes ——————☐————— several hours

Please click on the line below in the position that best describes how much time you spent in the sun in the past:

never ————————☐——— frequent

*Skin Condition*

16 Facial Skin Firmness

Please click on the line below in the position that best rates your facial skin firmness:

firm ————☐———————— very unfirm

17 Skin Texture

Please click on the line below in the positions that best describes your skin's texture where you will be applying your products:

rough ————☐———————— smooth variable ——————☐—————— even

18 Dark Spots

Please click on the line below in the position that best rate your dark spots:

| very few | Face ———————☐—————— | very many |
| | Hands ——————☐——————— | |
| | Forearms ————————☐———— | |
| | Chest / Back —————————☐——— | |

FIG. X3-D

(19) Please indicate below which of the following are of concern to you. You may click as many boxes as necessary.

Skin Concerns

- Acne
    face
    chest / back

- Excessive Oiliness
    forehead
    nose
    cheeks
    back

- Dark Spots
    face
    hands
    forearms
    chest / back

- Skin Redness
    cheeks
    nose
    hands

- Itchy, Scaly Skin
    face
    arms / legs
    hands

- Loss of Firmness
    cheeks
    neck

- Fine Lines and Wrinkles
    forehead
    eyes
    mouth area

- Puffiness Under Eyes

- Dark Circles Under Eyes

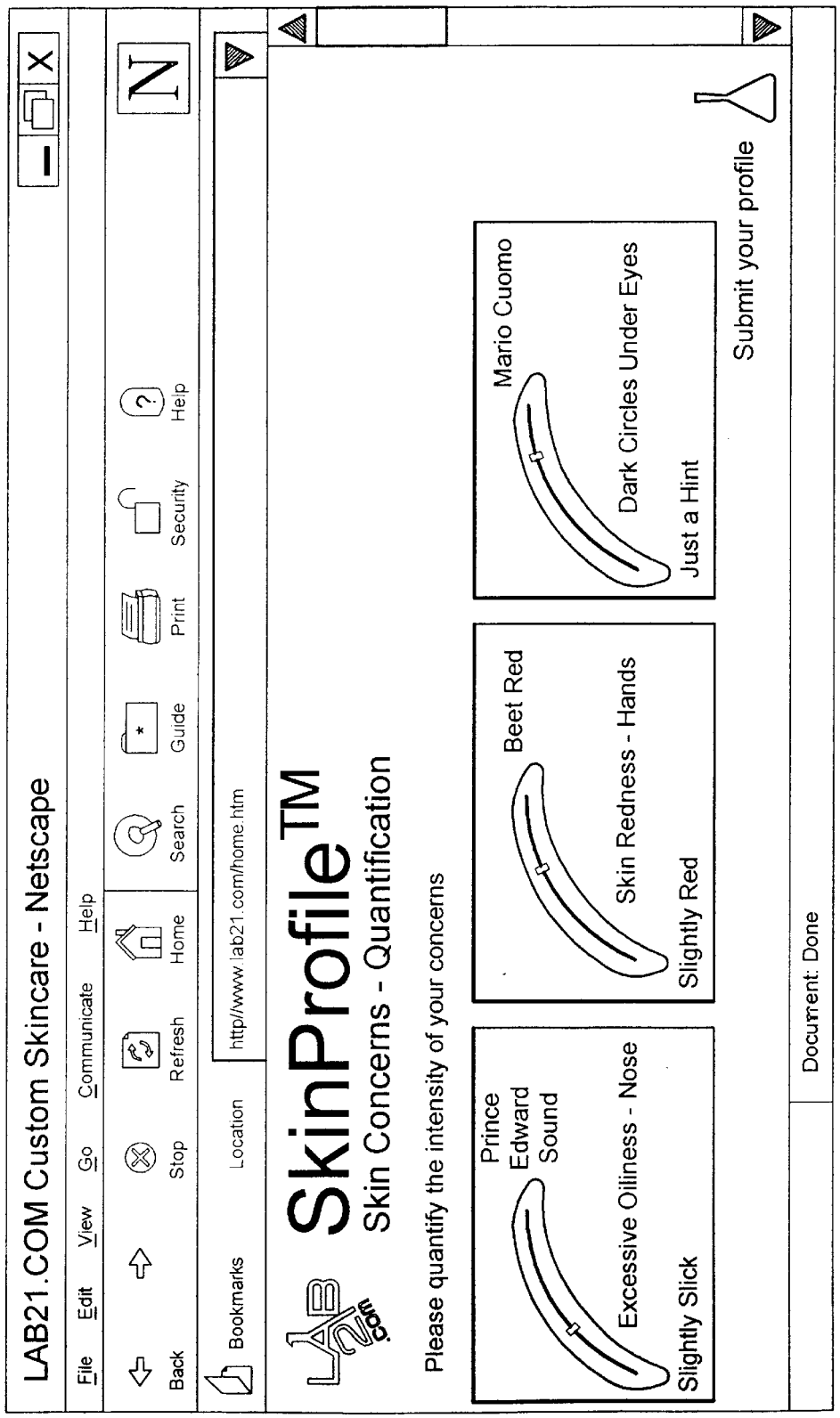
FIG. X3-E

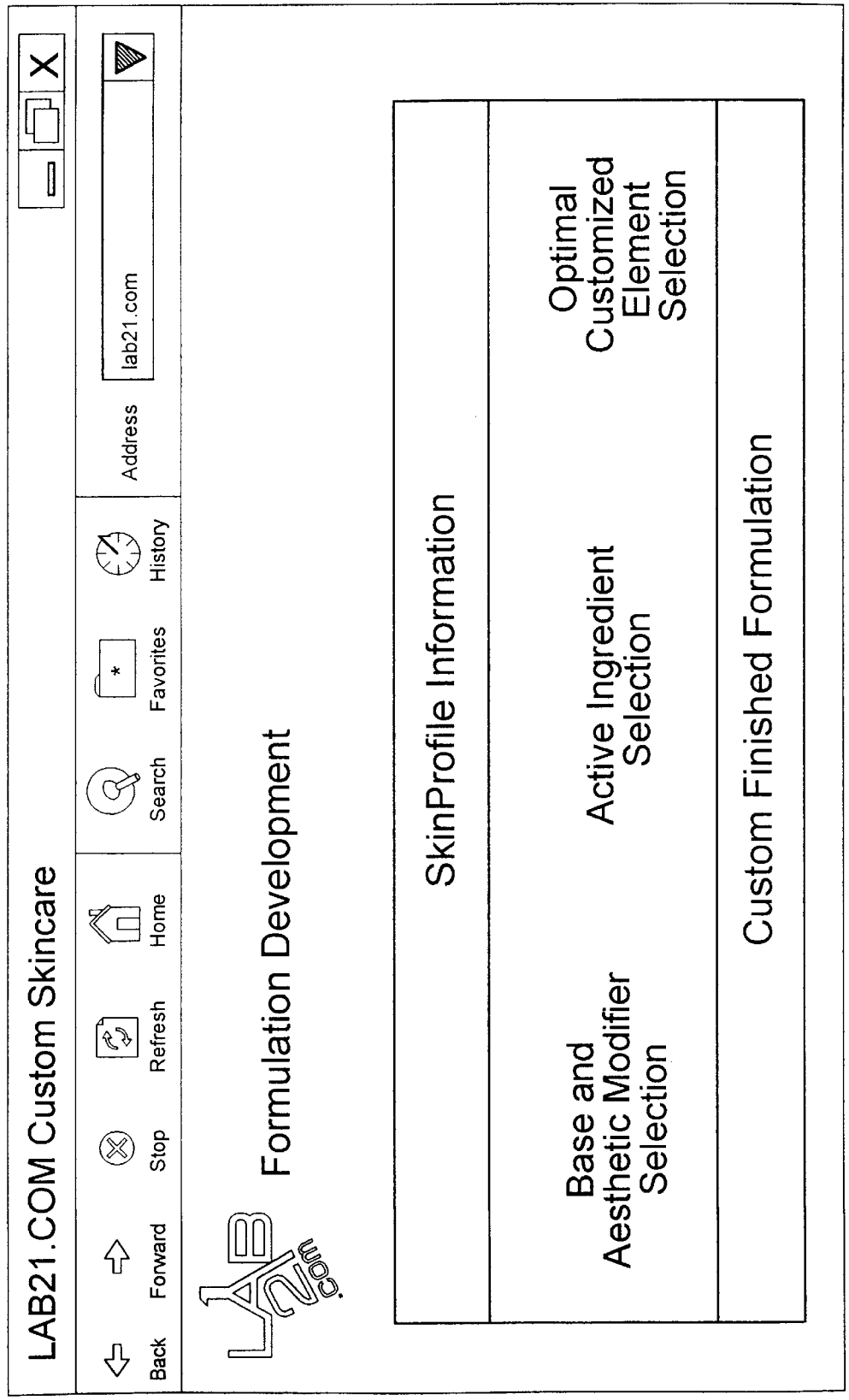

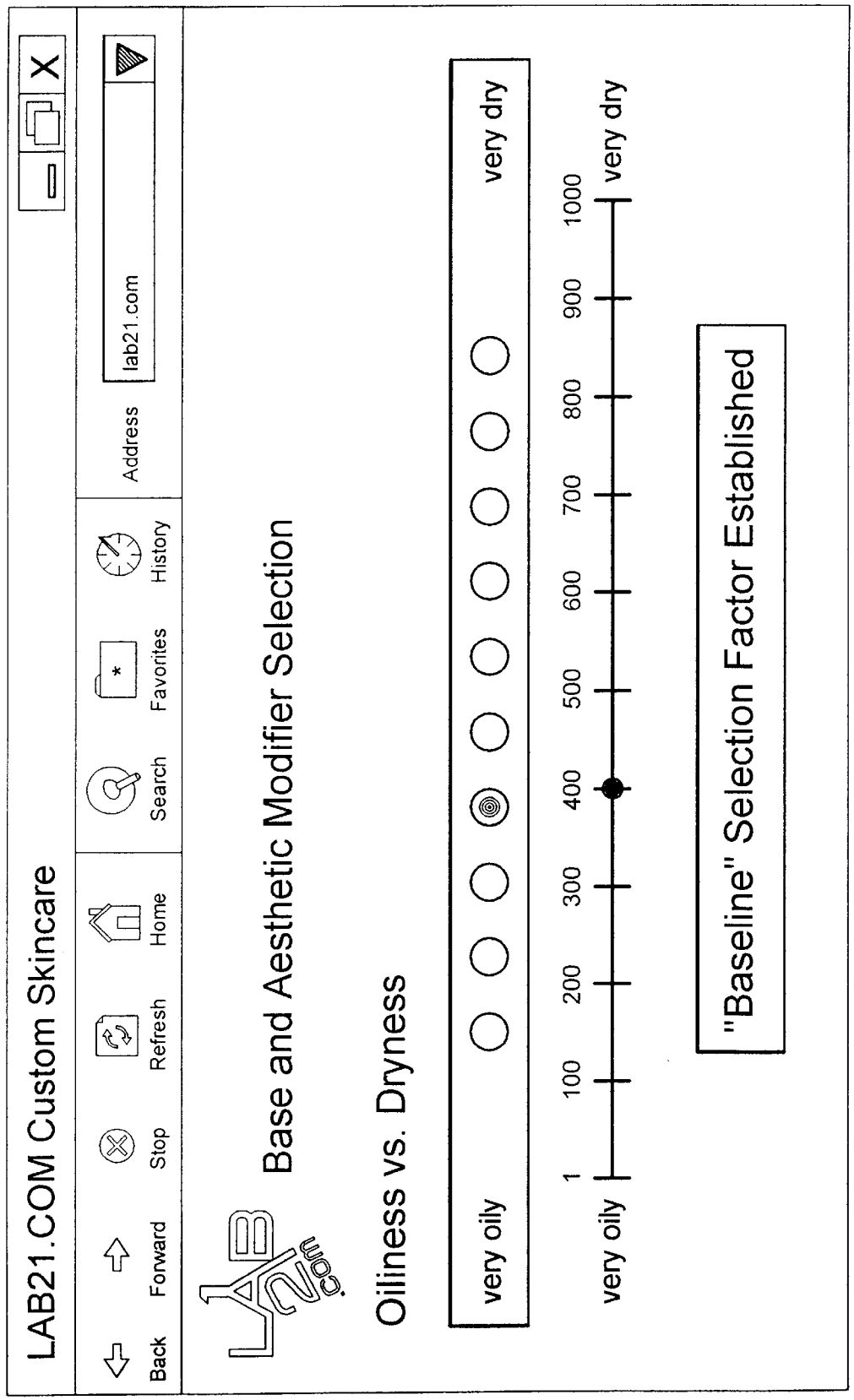
FIG. X5

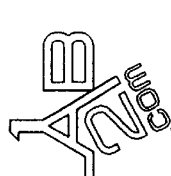

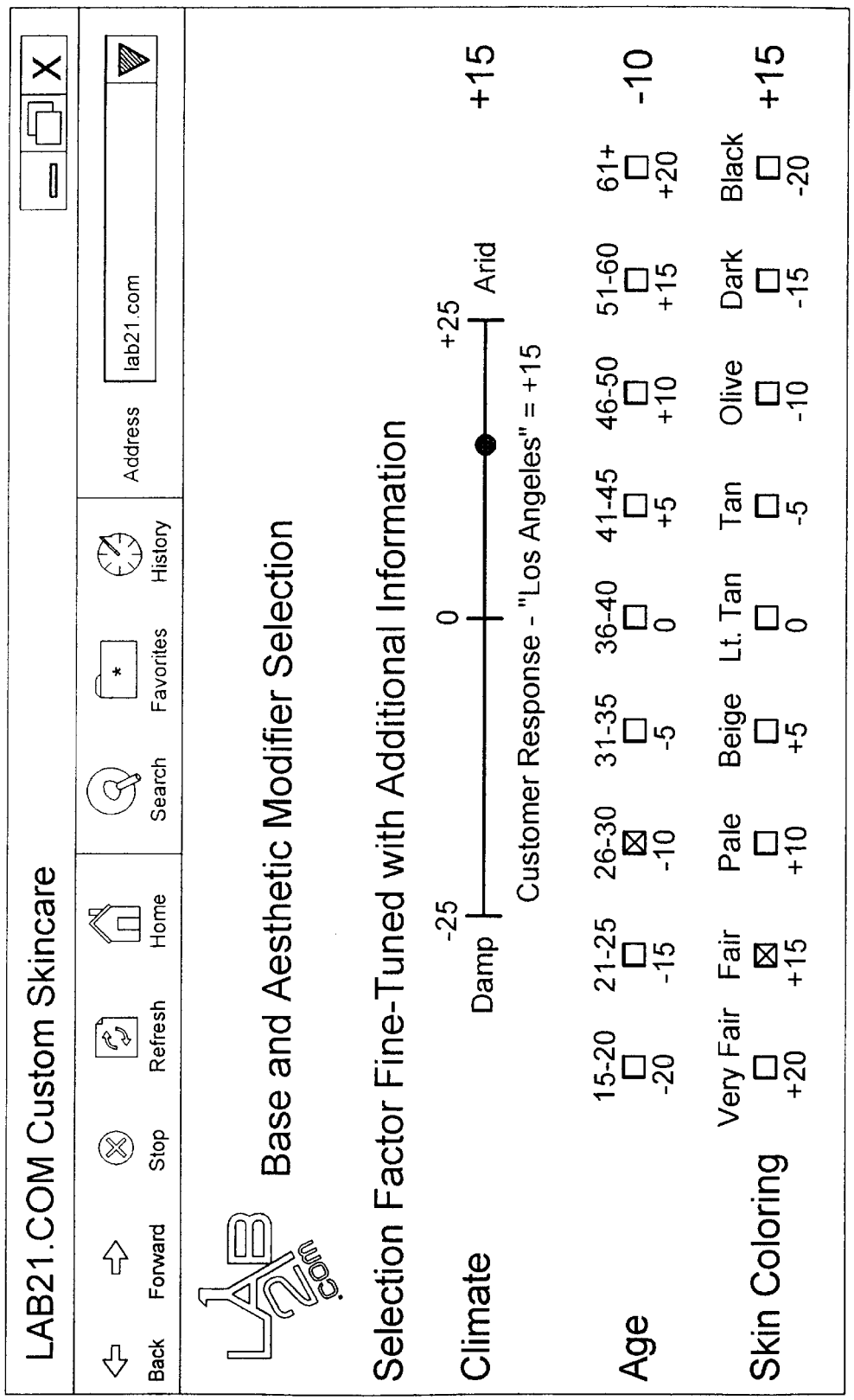

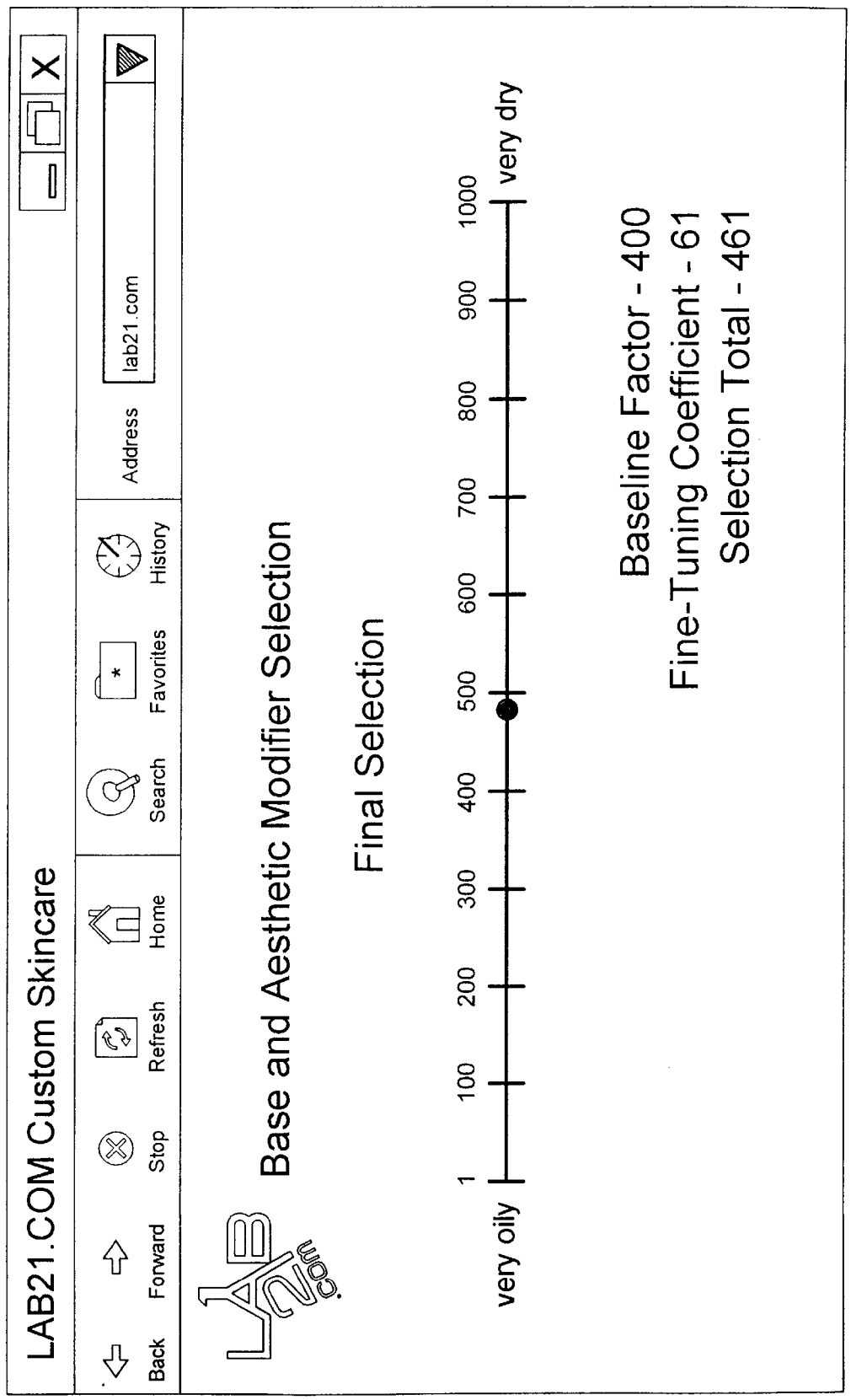
FIG. X8

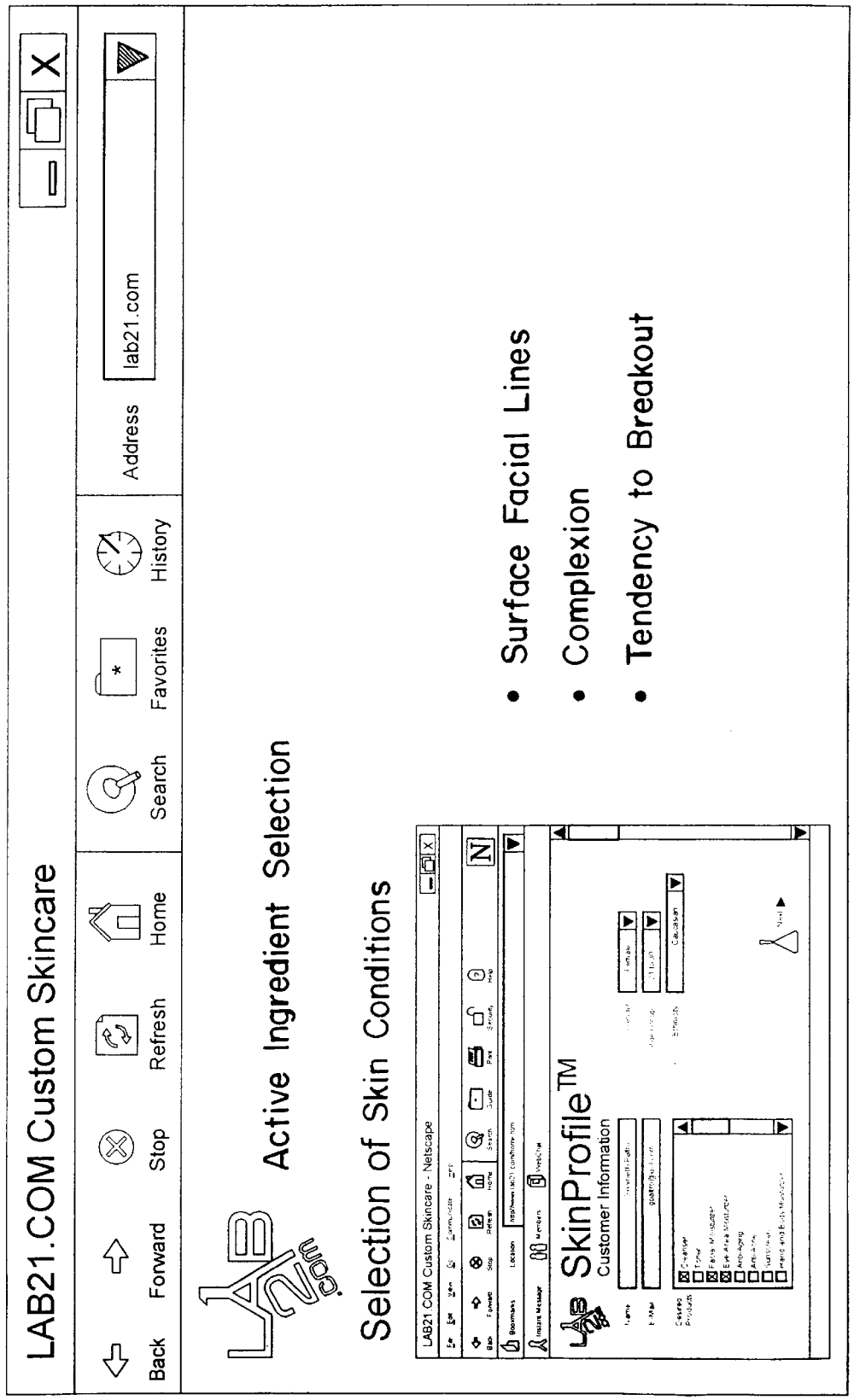

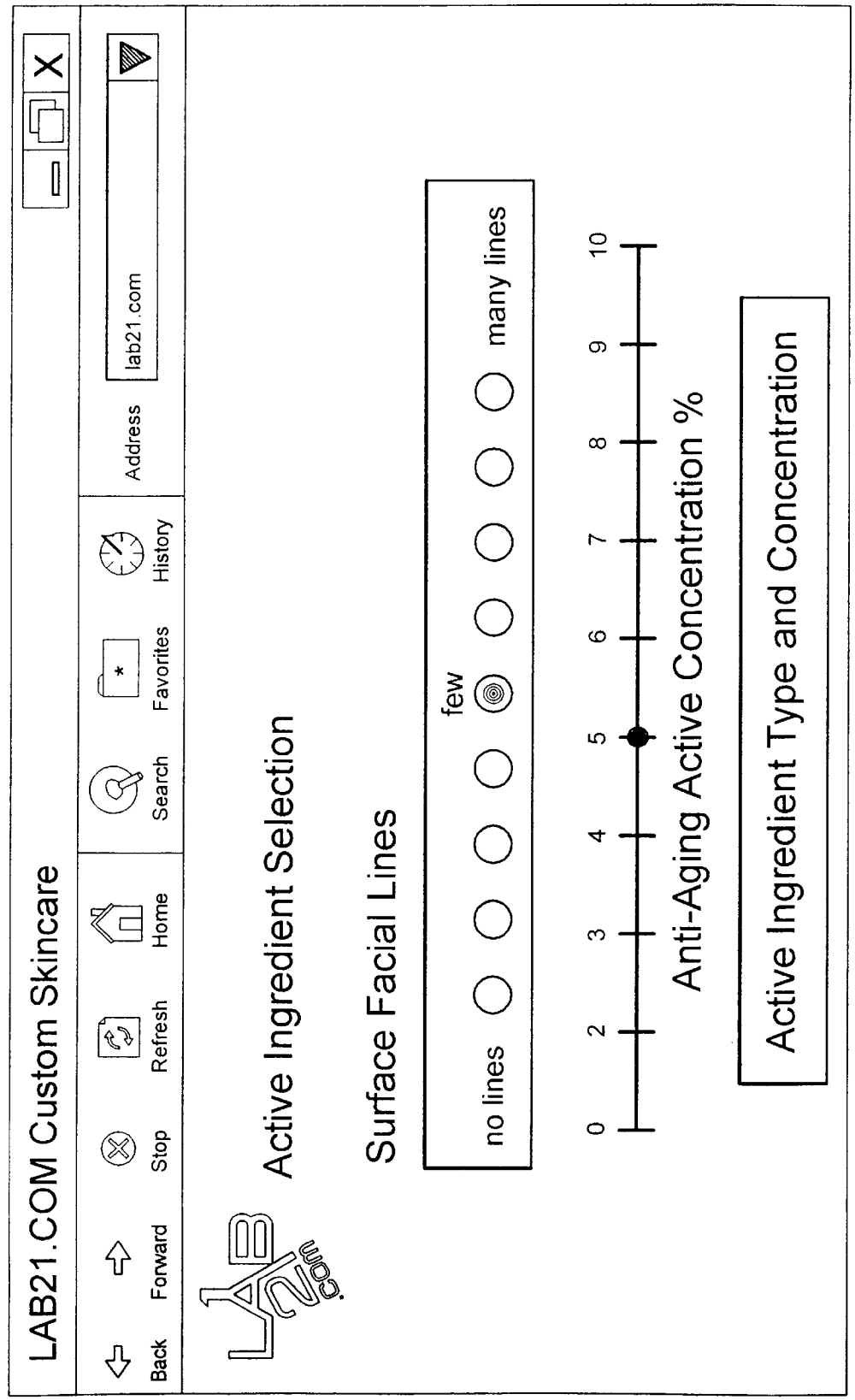

FIG. X11

LAB21.COM Custom Skincare

Active Ingredient Selection

Pigmentation even ○ ○ ◉ ○ ○ ○ ○ mottled

Tendency to Breakout never ○ ○ ○ ○ ○ ◉ ○ always

Active Ingredient Type and Concentration

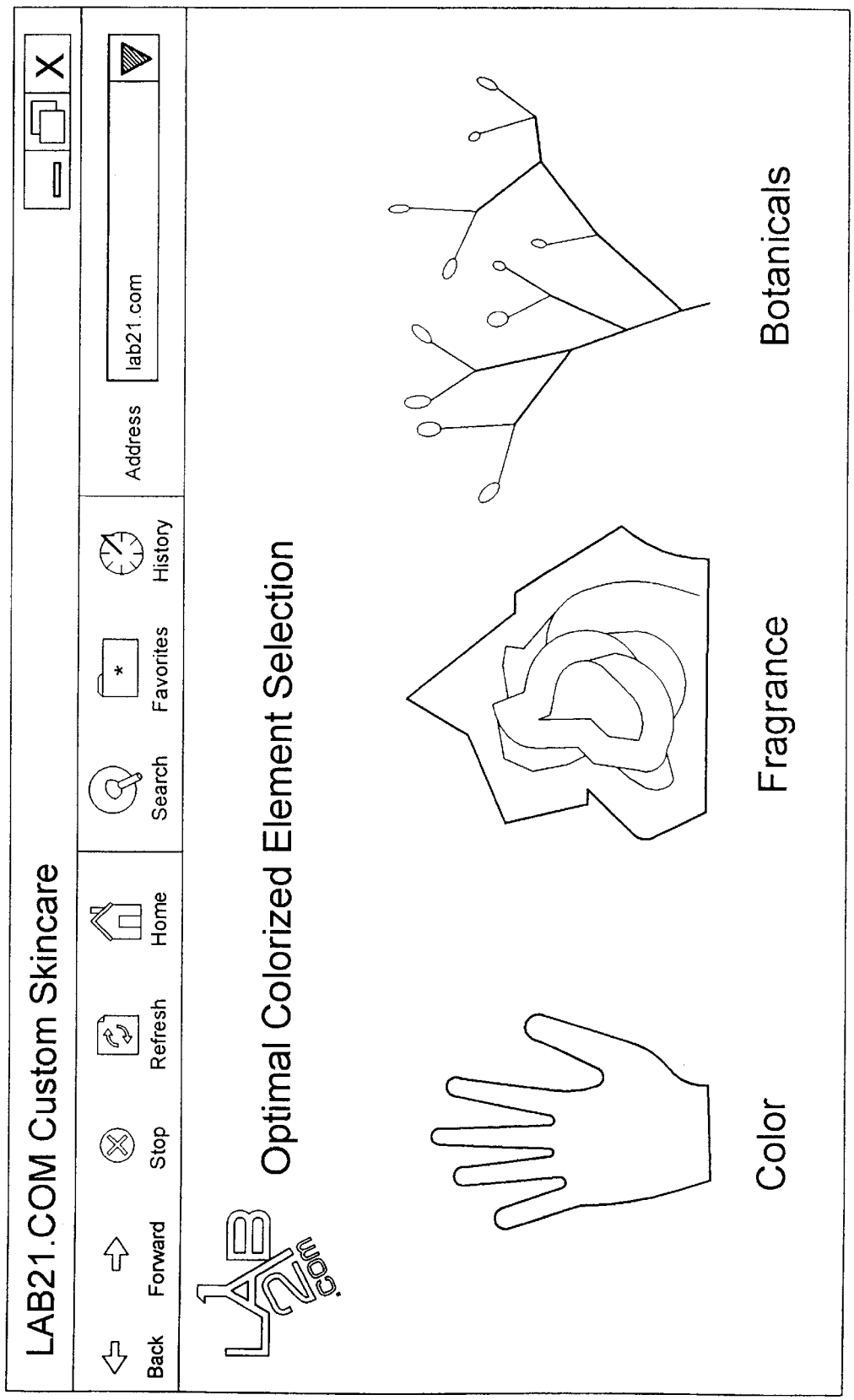

METHOD FOR PRODUCING CUSTOMIZED COSMETIC AND PHARMACEUTICAL FORMULATIONS ON DEMAND

This application is a continuation of International Application Serial No. PCT/US01/03168 and claims the benefit of U.S. Patent Application No. 60/179,057, filed Jan. 31, 2000; U.S. Patent Application No. 60/191,878, filed Mar. 23, 2000; and U.S. Patent Application No. 60/216,847, filed Jul. 7, 2000, all of which are hereby incorporated by reference.

FIELD OF THE INVENTION

This invention relates to a method and system for producing customized cosmetic and pharmaceutical formulations on demand.

BACKGROUND OF THE INVENTION

It is becoming increasingly desirable for a company to manufacture products which are customized to the user's wishes and needs. One product that has largely resisted this trend, however, is cosmetics, particularly high quality topical lotions. Generally, a company offers only a limited number of lotion formulations for sale. These formulations are selected to provide the largest possible consumer base. As a result, consumers with special needs or desires are often marginalized and cannot find the products they desire for a reasonable price.

Several attempts have been made to provide for customized cosmetic products at a point of sale location. For example, Clinique has implemented a computer aided questionnaire system which selects the company's product that most closely matches the user's characteristics. However, the products are all pre-manufactured and there is no customization.

U.S. Pat. No. 5,622,692 to Elizabeth Arden discloses a method and system for customizing facial foundation products. The system uses an electronic sensor to determine the skin-type of a customer and provides that information to a computer system which formulates and then initiates the mixing of an optimal foundation product. However, the disclosed system is directed primarily to adjusting the color of a premixed foundation base and not to cosmetic products generally. Moreover, the '692 patent does not address the method of determining the customized formulation, nor does it address how to manage the formulation when the customization process permits alteration of the entire composition, as opposed to simply color.

SUMMARY OF THE INVENTION

A method and system for selecting and producing a customized cosmetic or pharmaceutical formulation is disclosed below. The system can be implemented in an Internet based system or a stand-alone version, such as a Kiosk. An improved method of custom formulation is presented which utilizes the user's preferences and profile, as well as external factors. The customized formulation can be directed to a manufacturing facility for on-demand production. Alternatively, a printout of the formulation can be provided for subsequent use at point-of-sale locations, such as a cosmetics store or a pharmacy. The custom formulation software can also be provided in conjunction with a cosmetics manufacturing kit for use in home or business application.

BRIEF DESCRIPTION OF THE DRAWINGS

The foregoing and other features of the present invention will be more readily apparent from the following detailed description and drawings of illustrative embodiments of the invention in which.

FIG. X1 is a high level representative flow diagram of a particular implementation of various aspects of the invention;

FIG. X2 shows a representative computer screen for receiving customer profile information used to determine base and aesthetic modifiers for use in the custom composition FIGS. X3A–X3E are illustrations of a detailed questionnaire used to establish a customer profile and the customer's concerns that the product is to address;

FIG. X4 is a figure illustrating the various steps which are used to generate a customized formulation;

FIGS. X5–X8 illustrate a method for tuning a formulation selection in accordance with profile and environmental factors;

FIGS. X9–X11 illustrate use of user input used to select active ingredients for use in the composition; and FIG. X12 illustrates various customized element selection options.

DETAILED DESCRIPTION OF THE PREFERRED EMBODIMENTS

Particular methods and systems for producing a customized composition for at least one of topical, oral, nasal, anal, ophthalmic, and vaginal application, which method is suitable for use in either a distributed Internet-based system or an on-demand kiosk manufacturing system will now be discussed.

Figure 1:
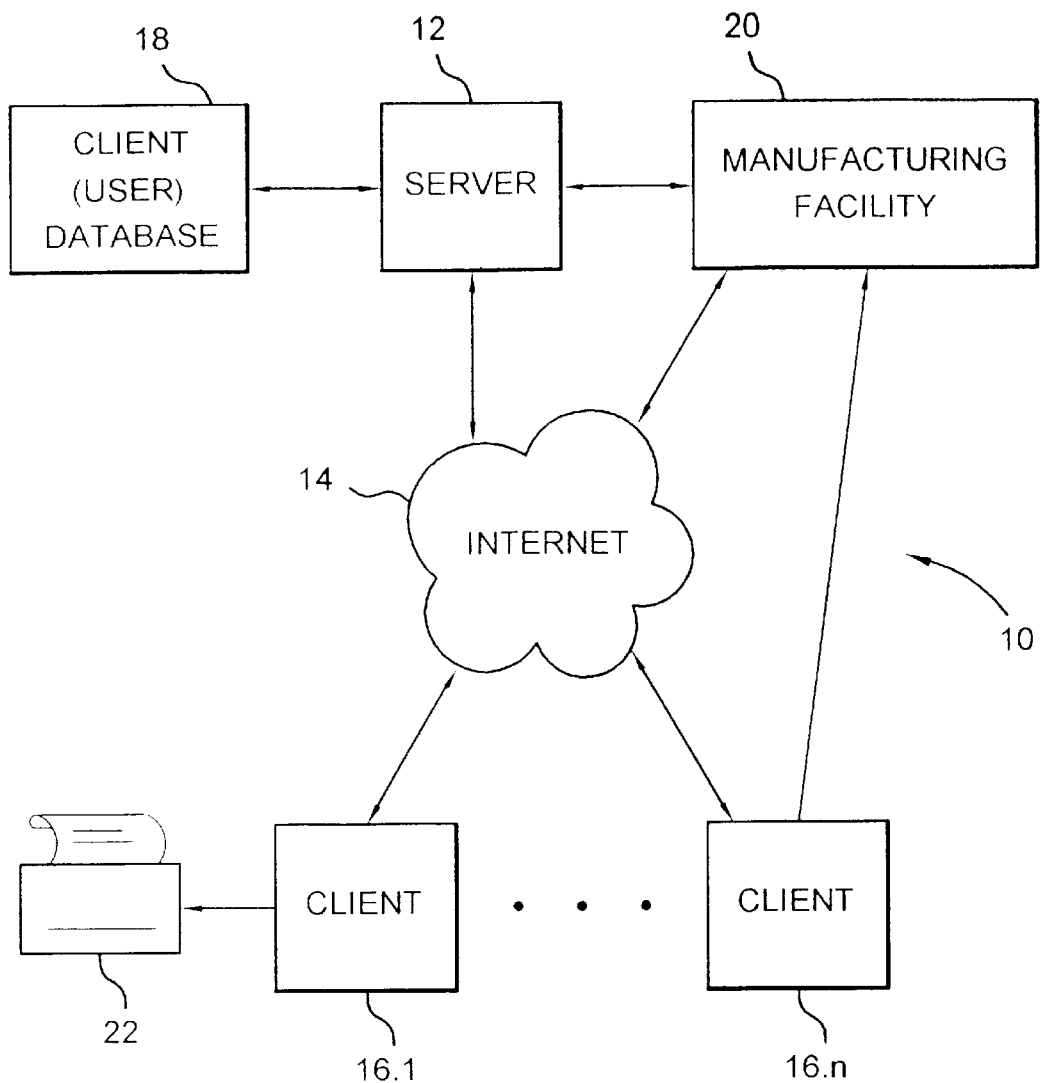
FIG. 1 shows an Internet-based system for providing customized cosmetic products on demand.

Turning to FIG. 1, there is shown an Internet-based system for providing customized cosmetic and pharmaceutical formulations on demand. The system 10 comprises a server 12 which can be accessed via a network 14, such as the Internet, by a plurality of clients 16.1 to 16.n. Preferably, the server is an HTTP server and is accessed via conventional Internet web-based technology. The clients 16 are computer terminals accessible by a user and may be customized devices, such as data entry kiosks, or general purpose devices, such as a personal computer. A printer 22 can be connected to a client terminal 16. The server is connected to a client database 18 and, either directly or indirectly through network 14, to a manufacturing facility 20.

The manufacturing facility 20 can be located proximate to the server 12 and be part of an overall customized ordering and manufacturing system. Alternatively, manufacturing facility 20 may be remotely located from both the server 12 and the clients 16. For example, if the system 10 is used by a dermatologist to develop a customized prescription cream, the formulation can be forwarded directly, such as via e-mail, to a manufacturing facility located in a pharmacy or hospital. In yet a further embodiment the manufacturing facility can be located proximate a client 16. This arrangement is particularly well suited for a kiosk-based on-demand manufacturing system, e.g., such as may be located in a point-of-sale establishment. These three potential connections to the manufacturing facility 20 are illustrated in FIG. 1. Although multiple manufacturing facilities located at different places can be provided, generally only one connection will need to be implemented in a particular embodiment of the invention.

Figure 2:
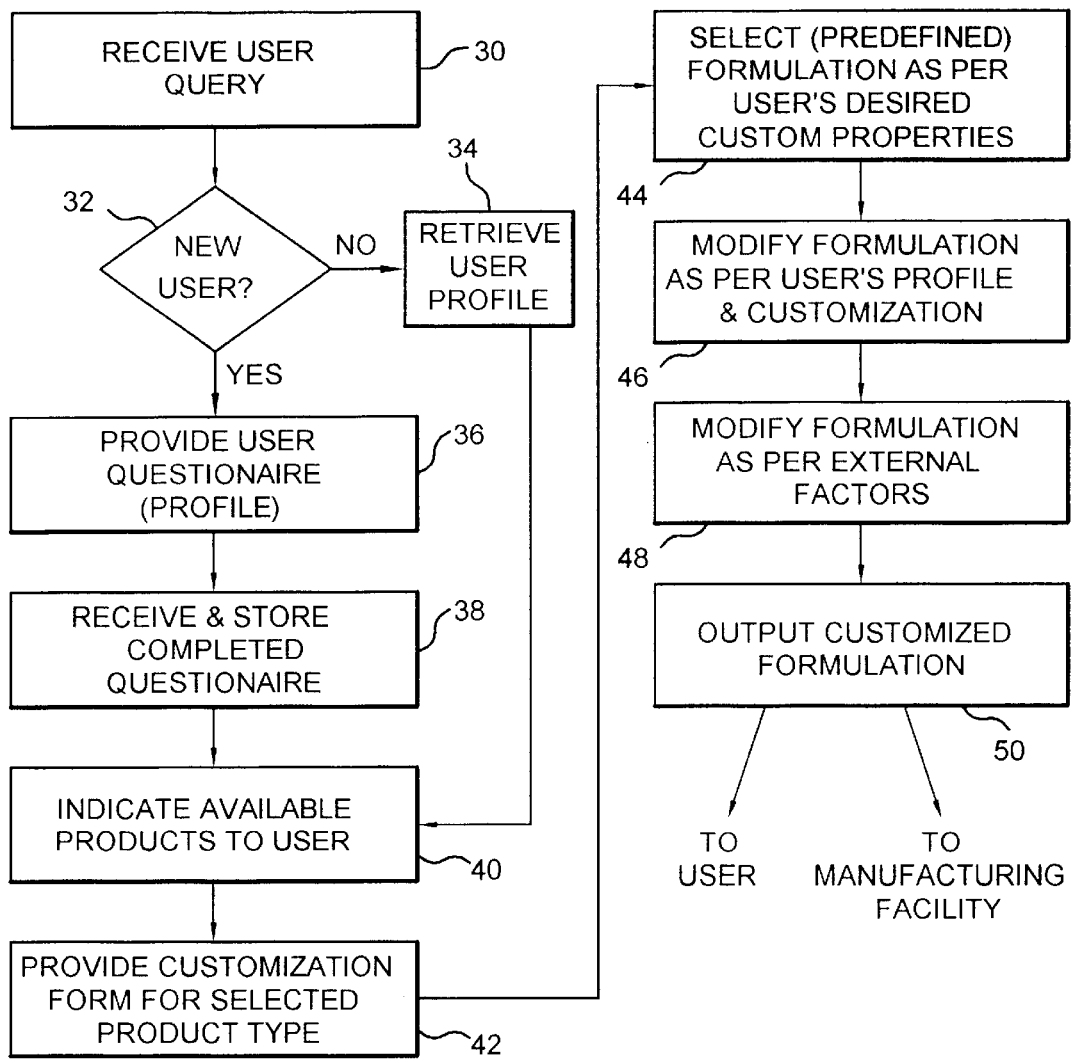
FIG. 2 is a flow diagram of the general operation of the server of FIG. 1.

FIG. 2 is a flow diagram of the general operation of a process executed by server 12. When a user accesses server 12 and indicates that they want to place an order for a customized cosmetic product (step 30), a determination is made regarding whether the user is new to the system or not. (Step 32). If the user has previously accessed the system and completed a user profile, at least some of the user profile is retrieved (step 34). Typically, the user will be asked to enter their ID, either directly on a keyboard or card reader, or indirectly, depending upon how the client terminals 16 are implemented and where they are located. For example, if the terminals 16 are located in a commercial establishment, customers may be issued access member or discount cards that can be swiped to gain access to the system. If a terminal 16 is a home computer, the user's ID can be stored as an Internet cookie which is automatically transmitted to the server 12 when accessed by the user. The user can be given the option of adding to or correcting their profile and storing the updated information.

If the user is new to the system, a user profile questionnaire is provided to the user. (step 36). The user profile includes at least that information which is useful for formulating a customized cosmetic product, such as one or more of the user's age, sex, race, skin type, skin color, allergies, etc. Additional profile information can also be requested for other purposes, such as directed advertising, discounts on related products or other purposes.

Once a completed questionnaire is returned, the new user is assigned a unique ID and the profile data is stored in the user database. The ID is communicated to the user and, in a card-based system, may be printed or otherwise encoded on an access card which is subsequently dispensed in accordance with conventional techniques. Depending on implementation, a user's profile can be stored on such a card, particularly cards using so-called "smart-card" technologies. In such as case, the information stored in the client database 18 can be limited or used for backup purposes only or perhaps eliminated entirely.

Once the user has accessed the system and provided their ID, the available products are communicated to the user and the user is asked to select the general type of product they are interested in, such as a sun-screen or moisturizer. The indication can be the same for all users. Preferably, however, the indication is modified in accordance with the user profile, and perhaps a history of prior orders, to emphasize products which may be of particular interest and remove items which are unlikely to interest the customer or feature them less prominently. Alternatively, the user can fill out a questionnaire and indicate their general product needs and the system can advise the customer of the correct products.

The user is then asked to select the general type of product of interest, if more than one is available, and subsequently indicate how they would like the product customized, either indirectly by defining their product needs, or directly, as in the case of a medical application, by specifying that certain compounds, such as medicinal agents, must be included in particular concentrations. (step 42). The type-selection and customization can be performed via a single questionnaire, or can be an iterative process as some customization factors may only be appropriate for specific product types. The factors which can be customized include, but are not limited those which effect the aesthetic quality of the product, the active ingredients or performance properties of the product, as well as other miscellaneous factors.

During the customization process, the user (preferably when the user is a pharmacist or medical practitioner), such as aloe. Specific customization of this type is particularly well suited for production of custom compositions which include pharmaceutical and therapeutic active agents. In such cases, the user can be permitted to specify the actual or relative quantity of the active agent to be added, for example a 10% Retin-A™ cream. Alternatively, and more preferably for non-medical uses, the user is prompted to select the desired characteristics of the product without particular regard for the specifics additives and quantities of those additives which are used to achieve that characteristic. For example, a user may request a moisturizing lotion which includes a sun-screen agent. In most instances, the user is generally unconcerned with which additive is used to achieve the requested characteristic and the system itself selects the appropriate effective amounts of particular additives to achieve the desired effect.

Some characteristics of the custom order can be specified according to a "performance scale" or strength. If a well established reference number for a property is available, such as the SPF number for sun screens, the user is permitted to specify that number. If, however, an established weighting is not widely known, the property can be specified on an arbitrary scale. For example, the "density" of a cream, can range a from very light and a low residual (zero) to very emollient with a noticeable residual (1000).

Customization of cosmetic compositions manufactured using a preferred and newly developed chemical process is discussed in more detail below.

Based on the properties and characteristics of the customized product specified by the user, and possibly the user's profile, an initial cosmetic formulation is selected. (Step 44). The formulation comprises a base composition to which one or more additives are added, such as active agents and adjuvants, the type of which and quantities are specified by the formulation. The initial formulation can be generated on-the-fly. Preferably, however, the specific additives and associated quantities are selected from a set of predefined formulations or partial formulations which generally cover the spectrum for the available customizable properties. In a preferred embodiment, the predefined formulations or additive specifications are defined on a coarser scale than the user is permitted to specify. Thus, while the user may be permitted to request a cream emolliency (e g., how oily the cream feels) on a scale from 0 to 1000, only 11 predefined additive specifications may be provided, corresponding to selections from 0 to 1000 at 100 point intervals. Courser specifications are preferred because it simplifies situations where different additives are required to achieve different attributes on the customization scale.

For example, additive A in varying quantities may be best suited to provide a sun screen having an SPF ranging from 2 to 4. However, adding enough additive A to achieve an SPF of 8 may compromise the aesthetic quality of the final product. Thus, it may be more appropriate to use additive B for the SPF range of 4 to 8 and additive C from the range of 8 to 20.

Once a formulation has been selected, it is modified using knowledge of how changes in the quantity of the various additives to the base composition effect the final product to provide a formulation which meets the user's specific customization selection. For example, there may be one base composition for acidic formulation, e.g., formulations having a pH of less than 4, and a different base composition for pH neutral formulations.

Continuing the SPF example, if the user has specified an SPF of 4.5, the closest predefined formulation may be for an SPF of 4 having a defined quantity Q1 of additive A. Based on knowledge of how the SPF varies with variations in the quantity of additive A, the amount of A in the formula is adjusted to achieve the desired SPF rating. In addition, further refinements to the predefined formula can be made in view of the user profile. For example, a pH adjuster might be added to adjust the final pH of the product as desired or needed.

Finally, the formulation can be further modified based on external factors, such as where the user intends to use the product, the time of year, local weather, etc. For example, if the user intends to use the product in the North East during winter, an area typically very dry, the formulation can be modified to include or increase the amount of an added moisturizer or the user can be prompted to select or reject such a modification. If the product is to be used in Florida during June, the system may suggest the addition of a sun screen or a higher SPF level. Preferably, the modifications based on external factors are proposed to the user and can be accepted or declined prior to being incorporated into the customized formulation.

As can be appreciated by those of skill in the art, because many various factors may be considered when customizing a formulation, an initial formulation may prove to be unsuitable once all of the additives have been identified. Thus, the formulation adjustment process can be iterative in nature wherein several modified formulations are evaluated until a suitable customized formulation is generated.

Once a final customized formulation is developed, it is output by the server (step 50) and directed to the appropriate location. If the user has requested that the product be manufactured, the order can be directed to the manufacturing facility 20. As discussed above, this facility can be located proximate to the server or client or remotely located from both.

Another preferred technique for generating a customized formulation is illustrated and discussed with reference to FIGS. X1–X12.

In this technique, a library of predefined partial formulations is provided, which formulations define the overall aesthetic quality of the customized product, such as its emollient quality. The predefined formulations are each assigned a respective value, such as zero to 1000. Preferably, the formulations are configured to provide essentially the same aesthetic quality even after the addition of up to approximately 10% or so of additional materials, which materials may include active and other elements. The initial formulation value is selected based on a rough scale of how dry or oily the user's skin is. The value is then tuned according to other profile factors to determine the formulation for the product which has the correct aesthetic features, e.g., to restore the user's skin to an ideal level between dry and oily. The final "tuned" value is used to identify the aesthetic portion of the customized formulation. The net effect of the tuning process is to adjust the initial course value to take into account how receptive the particular user will be to the selected aesthetic quality of the product since, for example, older skin generally needs more moisture than younger skin and men and women may have different acceptable levels of skin oiliness. The formulation is then augmented with selected active ingredients according to skin problems indicated by the user and possibly further augmented with various customized element selections. In addition, it should be recognized that other fine adjustments to the formulation may be needed. For example, a pH adjuster may be necessary when elements of the formulation would otherwise result in a product which is too acidic.

FIG. X1 is a high level representative flow diagram of this particular implementation of the invention. As shown, the user enters skin profile information via, e.g., a form viewable through an Internet browser This information is used to select the base and aesthetic modifiers, the active ingredient (s), and optional customized element selections.

FIG. X2 shows a representative computer screen for receiving customer profile information used to determine base and aesthetic modifiers for use in the custom composition. A wide variety of question may be asked, including how oily or dry the user's skin is, the climate where the product will be used and/or the present season, the user's age, ethnicity or complexion, and skin sensitivity. A detailed user profile and customization profile questionnaire is illustrated in FIGS. X3a–X3e.

FIG. X4 is a figure illustrating the various steps which are used to generate a customized formulation. As shown, first the user enters their skin profile information, such as via the questionnaire in FIGS. X3a–X3e. From this information, the aesthetic portion of the formulation is selected. The active ingredient(s) are then added to the formulation and finally any additional customized elements are added to produce the final customized finished formulation. It should be noted that the order in which the various aspects of the formulation are defined is not critical and the order can vary if, for example, the aesthetic modifier selection is dependent upon which active ingredients are used.

FIGS. X5–X8 illustrate a method for tuning a formulation selection in accordance with profile and environmental factors. Turning to FIG. X5, the initial user selection of how oily or dry their skin is used to make a course aesthetic formulation baseline selection. In the example, the baseline is a value of 400. As shown in FIGS. X6 and X7, the course formulation selection value is then tuned in accordance with the additional profile information provided by the user. The amount of tuning is based on predefined variations, such as are illustrated in the figures. Once all of the desired profile factors have been considered and used to generate tuning adjustments, the tunings are combined and used to generate the final selection of the aesthetic modifier formulation. In the present example, the course baseline value of 400 has been tuned to a final value of 461. This value is used to identify the predefined aesthetic formulation which has been selected to correspond to this place on the fine 0–1000 scale. Of course, the formulation could also be generated on-the-fly using a predefined set of relationships and formulas which define how the various aesthetic modifiers which are available affect the final product.

FIGS. X9–X11 illustrate use of user input which is used to select the type and quantity of active ingredients to be added to the formulation. In this embodiment, the active ingredients are selected in response to user information which describes the quality of their skin and possibly various problems. For example, the user can be asked to indicate how many facial lines they have. Based on their response a particular anti-aging and/or anti-wrinkle active ingredient can be selected along with the appropriate quantity of the agent in accordance with, e.g., a look-up table of predefined agents and quantities. If the user indicates that they have pigmentation issues, and anti-mottling agent is added to the formulation in the appropriate quantity. Similarly, if the user indicates that they have acne problems, an anti-acne agent is added. If sensitive skin is indicated, an anti-inflammatory agent can also be included in the formulation. Specific agents to select and the appropriate quantities will be known to those of skill in the art.

Figure 3:
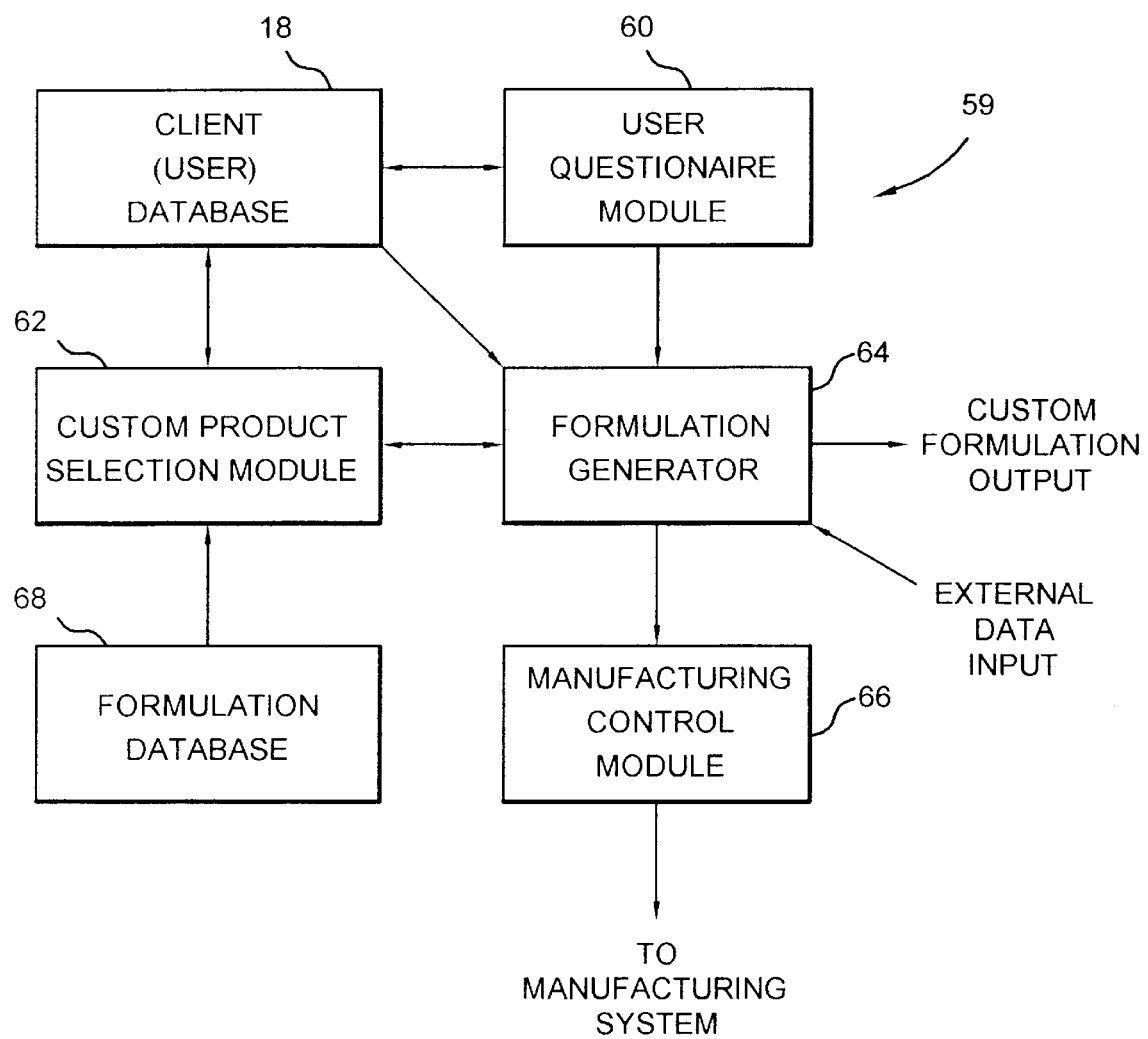
FIG. 3 is a block diagram of one embodiment of the software system for the server of FIG. 1.

Finally, as illustrated in FIG. X12, the user can select to include additional customized elements which address, e.g., the products color, its fragrance, and the addition of any additional botanical agents Turning to FIG. 3, there is shown a block diagram of one embodiment of a custom formulation software system 59 executed by server 12 which is suitable for implementing the method described above and illustrated in FIG. 2. As shown, the software system includes a user questionnaire module 60 which administers the user questionnaire and stores and accesses user profiles in the database 18. A custom product selection module 62 provides users of the system with appropriate customization forms for the product of interest, perhaps with reference to customization information stored in a formulation database 68. The custom product selection information is fed into a formulation generator 64 which, with reference to appropriate information in the formulation database 68, selects the predefined formulation, modifies it in accordance with the user's product selection and perhaps with the user profile stored in the database 18 and/or various external factors which are programmed into the system or provided via an external data port.

The formulation generator 64 can be configured to output the customized formulation to a manufacturing system which will then interpret the formula and manufacture the formula Alternatively, particularly when the manufacturing facility 20 is proximate the computer executing the software, a manufacturing control module 66 can be provided to interpret the formula and generate the appropriate data signals to directly control the manufacturing facility. As will be appreciated by those of skill in the art, a front end and various input/output systems (not shown) are also included in the software system as are appropriate to the specific environment in which the software is operating.

Figure 4:
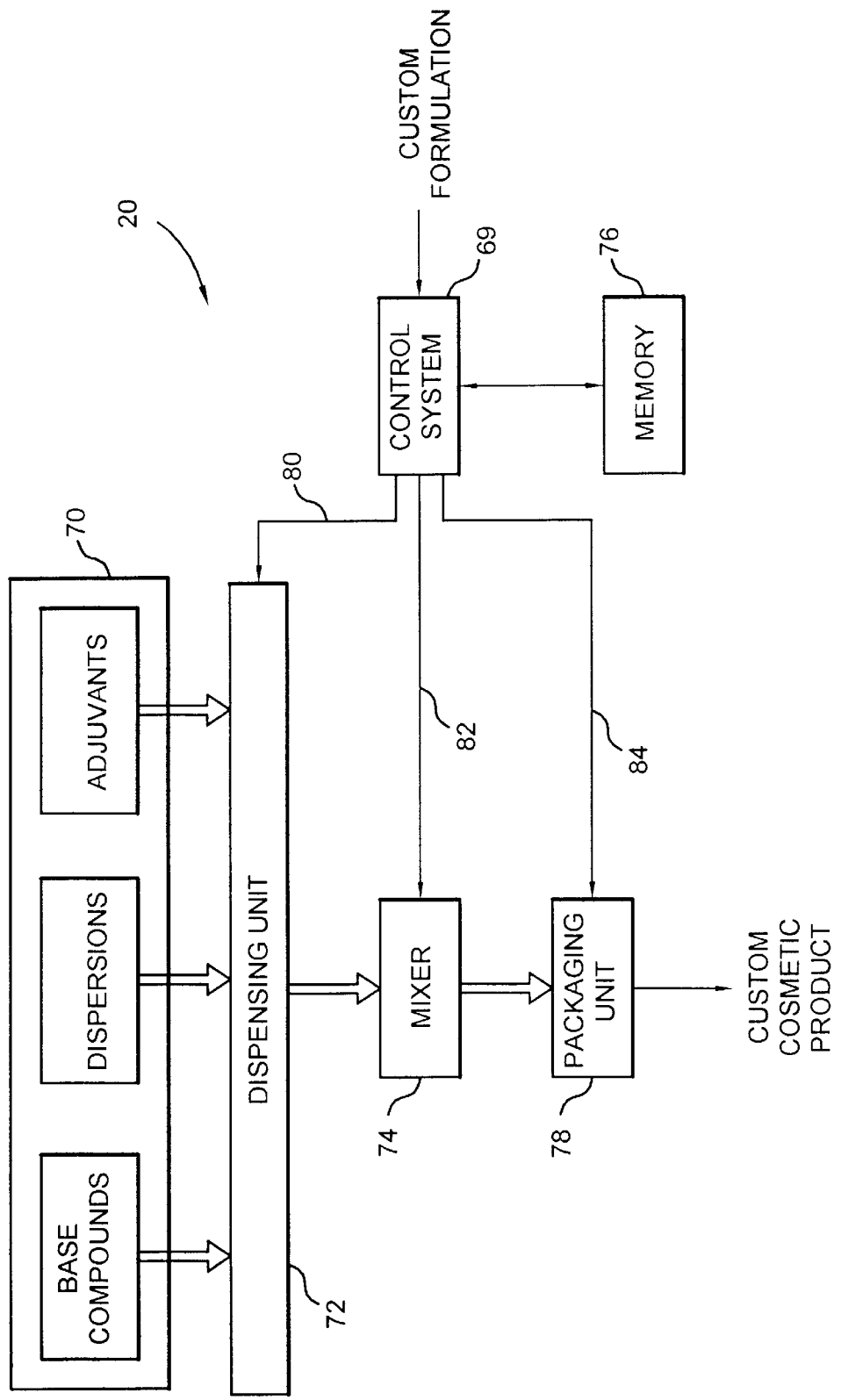
FIG. 4 is a block diagram of a representative manufacturing facility suitable for implementation in a point-of-sale location.

FIG. 4 is a block diagram of a representative manufacturing facility 20 which is suitable for implementation in a point-of-sale location. The manufacturing facility 20 receives a custom formulation in at control system 69, which can include a computer processor having a memory 76 and programmed to interpret a custom formulation in a manner similar to that of the manufacturing control module 66 shown in FIG. 3.

The manufacturing system 20 further includes a reservoir 70 which contains suitable quantities of one or more base compositions as well as various additives, such as active agents and adjuvants. A dispensing unit 72 dispenses measured quantities of one or more of these materials in accordance with control signals 80 generated by the control system 69. The dispensed materials are combined with a mixer 74 operated via control signal 82 from the control system 69. The mixed product is then dispensed, e.g., by a packaging and labeling unit 78 controlled via signal 82. The specific pieces of hardware used to implement manufacturing system 20 depend on the scale of the device and where it is implemented, e.g., a large-scale manufacturing plant as compared with a small device housed in a stand-alone kiosk. Various manufacturing devices of this type are known to those of skill in the art and therefore specific components of the system are not discussed further herein.

Figure 5:
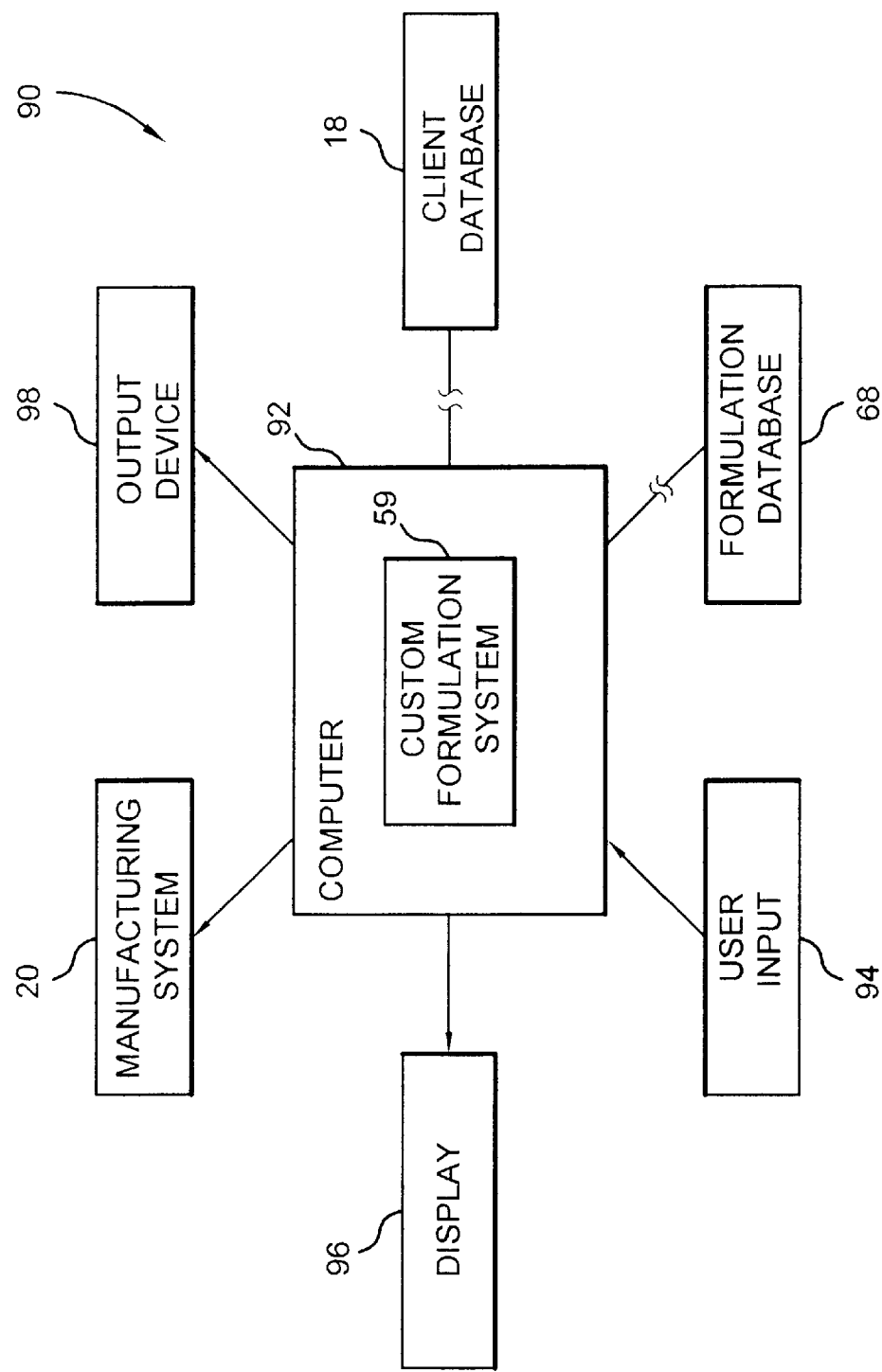
FIG. 5 is a block diagram of a stand-alone implementation of the present invention.

In the above embodiments, the customization method was discussed with regard to a server-based implementation. However, the customization system discussed above can also be implemented on a computer system which is local to the user. Such a stand-alone system 90 is illustrated in FIG. 5. As shown, the system 90 includes a computer 92 which is used to implement a custom formulation system 59 analogous to that shown in FIG. 3 and discussed above. Computer 92 has at least one user input 94 and a display device 96. The computer 92 can drive a manufacturing system 20 and/or an output device 98, such as a printer (22). Other devices, such as a credit-card reader 100, scanner, audio output 102, modem, etc., can also be provided. The client database 18 can be stored on a local storage device or it can be located in full or part, or possibly mirrored, on a remote storage facility which is accessed, e.g., through a network, such as the Internet. Similarly, the formulation database 68 can be located in full or part locally or remotely.

Figure 6:
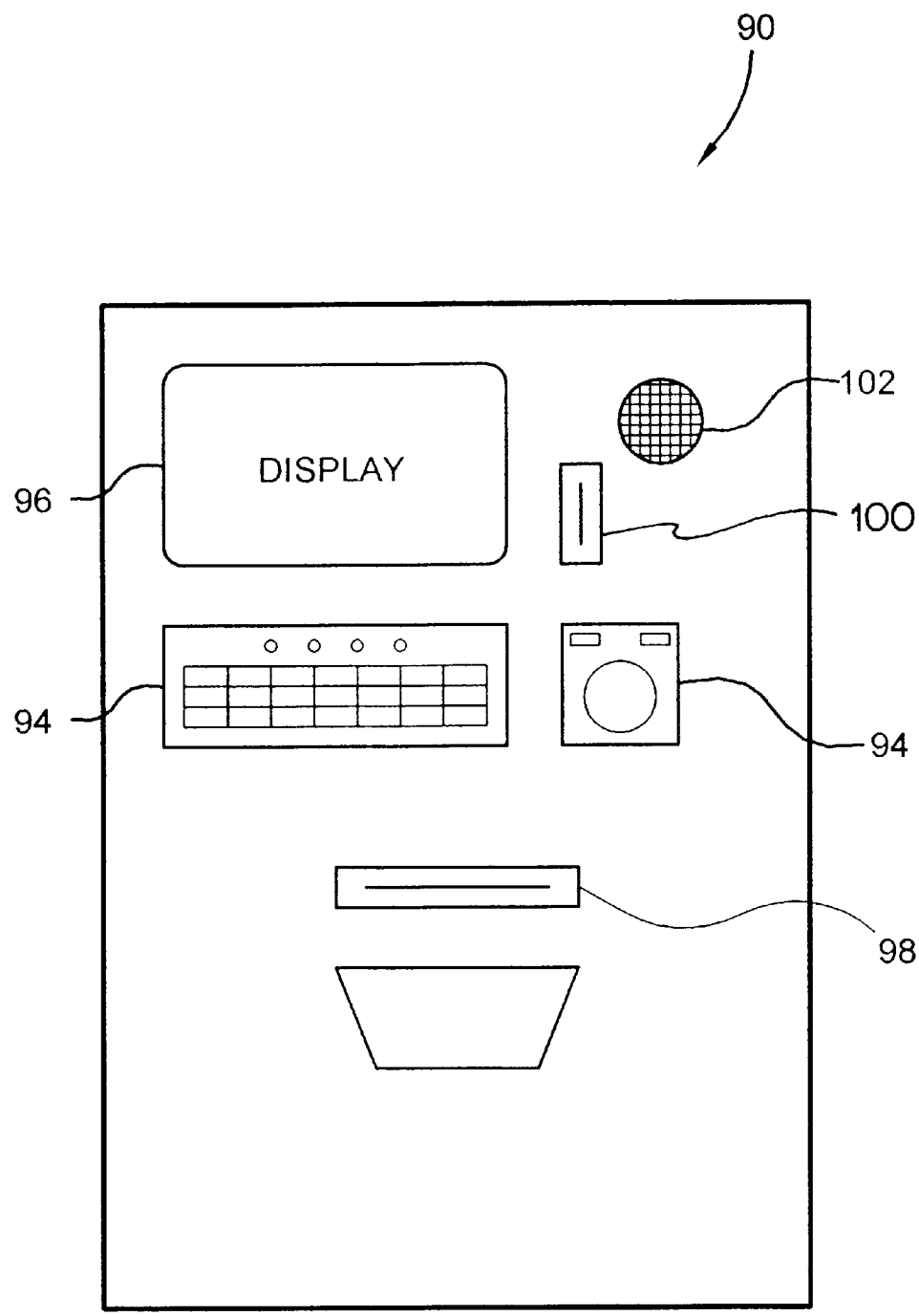
FIG. 6 is an illustration of an on-demand kiosk system suitable for implementing the present invention.

In one implementation, the stand-alone system 90 is implemented as a kiosk manufacturing system, such as shown in FIG. 6, which is suitable for use in a point-of-sale establishment, such as a cosmetics counter in a department store. In another embodiment, system 90 is implemented on a personal computer, perhaps customized, which can be used wherever custom cosmetic formulations are needed.

It should be appreciated that for small-scale implementations, the client database 18 may contain information on one or possibly a few users. Further, depending on how many user profile data points are used during the customization process, the client database could be eliminated entirely and the user simply required to enter the appropriate information each time the system is used. If the information is not entered, then customization based on user profile is simply skipped.

In yet a further embodiment, suitable for use in either the server or stand-alone system, the customized formulation is not automatically routed to the manufacturing facility and, in fact, a manufacturing facility need not even be connected to the system. Instead, the formulation is directed to a printer 22 or other output device, such as a display, so that a printout of the customized formulation is generated. The formulation can also be stored on a user-card if one is provided.

The formulation output is essentially a recipe for making the customized product. Because the customized product can be mixed by hand, partially or fully, such a system can be implemented in conjunction with a custom cosmetic kit wherein the various additives and base compositions are provided separately and measured and mixed by the user in accordance with the formulation output by the system.

Figure 7:
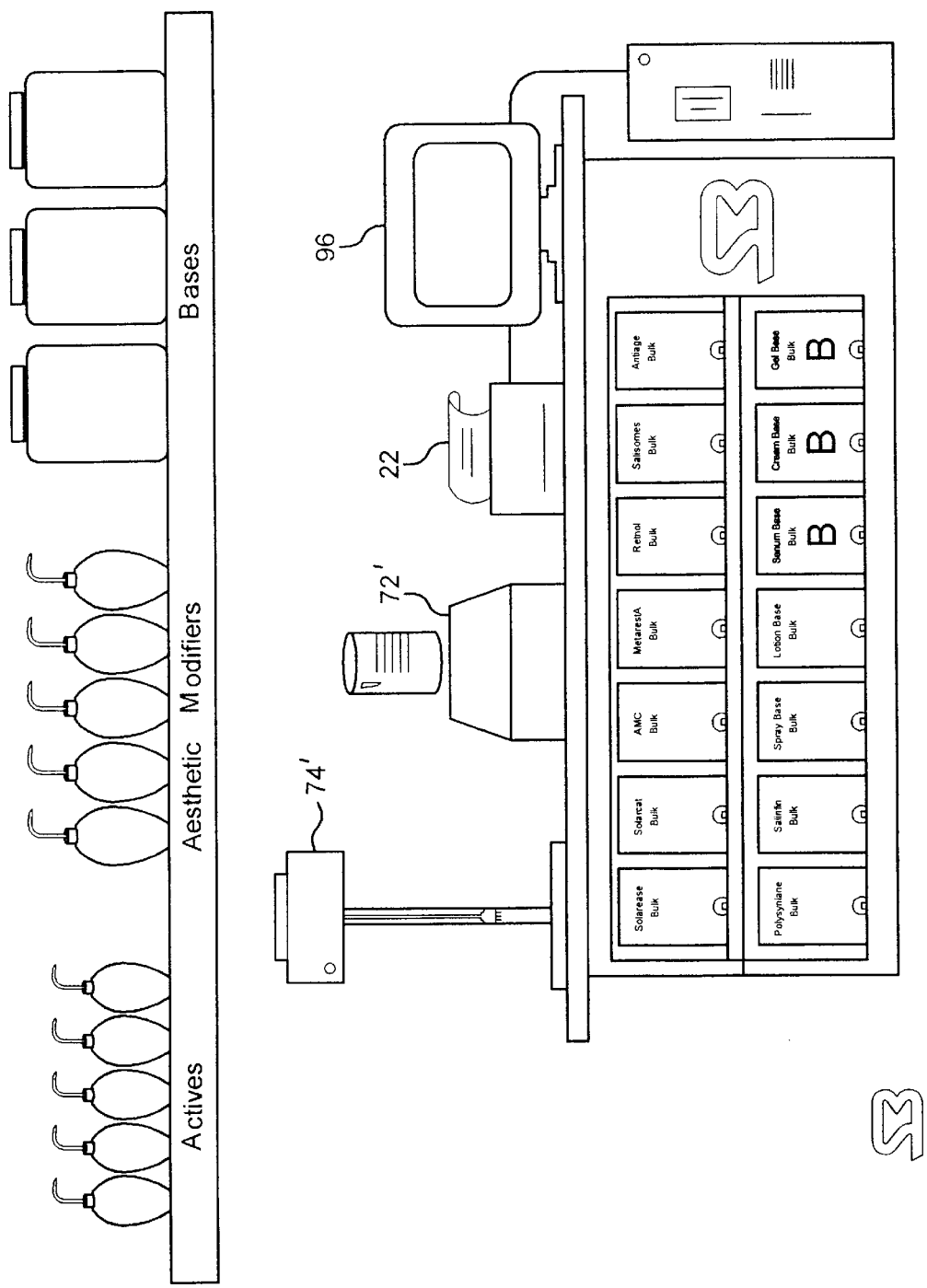
FIG. 7 is a diagram of a manual mixing station and a customized formulation system according to an embodiment of the invention.

For example, as shown in FIG. 7, the computer 92 outputs the custom formulation on display 96 or printer 22. The custom product can then be manufactured by hand in accordance with the formulation using, e.g., measuring device 72' and mixer 74'. Preferably, the base compositions and additives are of a type which can be easily mixed and a final product prepared in a short period of time, e.g., on the order of 1–10 minutes. Specific chemical composition most suitable for this use are described in detail below.

Figure 8:
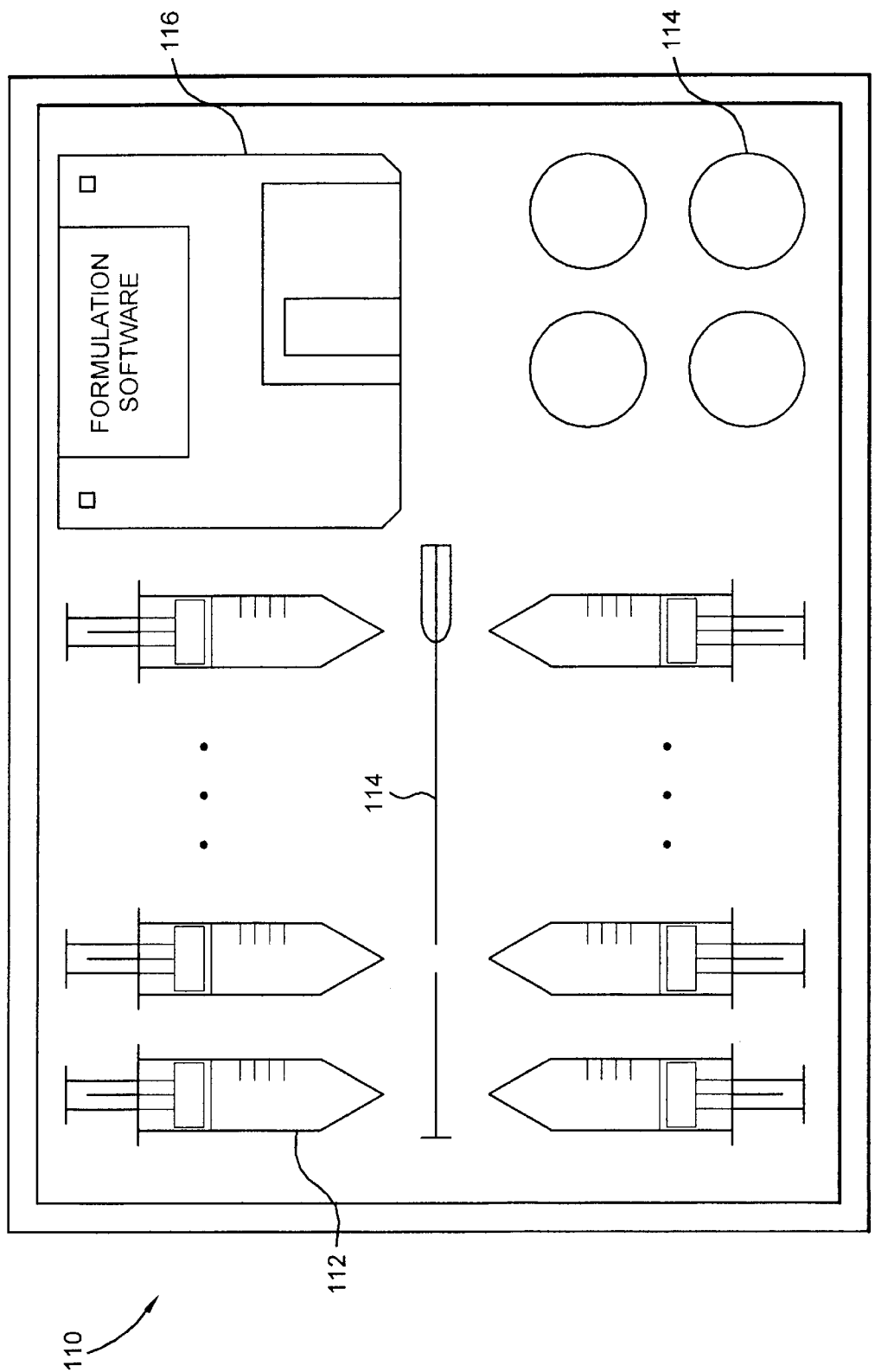
FIG. 8 is a diagram of a custom cosmetic manufacturing kit including materials and software according to various aspects of the invention.

The system illustrated generally in FIG. 7 is also suitable for implementation as a "make-your-own" cosmetics kit for use, e.g., in the home. Such a kit 110 is illustrated in FIG. 8. Kit 110 includes a plurality of additives in containers 112, such as pre-measured single-use ampules or multiple-use syringe dispensers with volume measurement indicia thereon. A plurality of containers for mixing the custom cosmetics can also be provided. The containers 112 can be empty or may contain a measured quantity of base composition into which the additives can be dispensed. A suitable mixing wand may also be included. Finally, a computer disk 116 or other appropriate media can be included on which an appropriate version of the custom formulation software system 59 is stored. Users of the kit would install the software on their personal computer, enter the properties of the cosmetic they are interested, and possibly user profile and external data, and then simply follow the directions provided in the custom formulation. Preferably, the software system limits the available formulations to those which can be produced using the additives provided in the kit and other additional additives which may have been separately obtained by the user. It can be appreciated that the kit need not come with the software if the formulation system is available to the user via the Internet. Alternatively, the kit can include a questionnaire that the user can fill out and, with the use of a scoring guide, determine an appropriate formulation to use from a look-up table. This embodiment has the advantage of not requiring a computerized implementation, although the formulation selection process may not be as accurate.

In yet a further embodiment, the custom formulation is provided to the user as a printout even if the user does not have direct access to the manufacturing facility. For example, the kiosk 90 of FIG. 6 can be implemented without a connection to an internal or external manufacturing facility. Similarly, the computer system of FIG. 7 can be operated without the presence of the components needed to produce the customized cosmetic product. The custom formulation printout can then be brought to a manufacturing facility, or a location where the specified formulation can be prepared by hand.

A printout-based system is particularly well suited for use in a retail establishment since the kiosk or stand-alone computer can be implemented without a manufacturing facility and, therefore, without immediate concern for receive appropriate payment. For example, the system could be placed adjacent a cosmetics counter in a department mall or a store or accessible via the Internet, such as illustrated in FIG. 1 and discussed above. A user of the system, which could be made available without charge, would follow the on-screen directions to define their custom product and then receive a printout of the customized formulation, perhaps with a price list for various sized preparations of that formulation, the cost of various ingredients (since some are more costly than others). The printout can also indicate locations where the product could be mixed for them. The user would then bring the formulation printout to an appropriate sales clerk who will mix the formulation in accordance with the printout (either by hand or with the aid of an automated manufacturing facility) and accept payment. Such a printout-only system can also be used by a doctor to generate a formulation for a prescription product. The custom formulation can be printed on prescription Rx, signed by the doctor, and then given to the patient to be brought to, e.g., a pharmacy for custom manufacture.

According to a preferred embodiment of the invention, the formulation for topical, oral, nasal, anal, ophthalmic, or vaginal application comprises a base composition and at least one additive. The formulation may be a cream, gel, lotion, serum, or spray. The base composition comprises a rheology modifying agent and water. Preferably, the formulation contains at least one dispersion comprising suspended particles of a hydrophobic active agent, a hydrophobic adjuvant, or a combination thereof. Typically, besides the base composition, the formulation only contains water-soluble ingredients and/or dispersions of hydrophobic active agents and/or hydrophobic adjuvants. Generally, hydrophobic ingredients which are not in the form of a dispersion are not included in the formulation, or at least not in any substantial amounts.

The formulation is preferably substantially free of emulsifying surfactants. This results in a formulation which does not irritate or minimally irritates a person's skin when applied. The formulation preferably comprises less than about 3% by weight and more preferably less than about 1% by weight of emulsifying surfactants, based upon 100% weight of total formulation.

The formulation may be prepared by mixing the aforementioned base composition and the additives. Mixing may be performed with a propeller mixer or manually, i.e., by hand. Since the formulation is simple and quick to prepare, custom cosmetic and pharmaceutical formulations may be prepared at the point of sale for customers in minutes.

Mixing is generally performed at a temperature of from about 15 to about 30° C., preferably at a temperature of from about 20 to about 30° C., and most preferably at ambient temperature. Since the hydrophobic active agent or hydrophobic adjuvant is added to the base composition as a dispersion, heating and other expensive processing steps are not required to obtain a homogenous final formulation. Preferably, the formulation is not heated or prepared with heating.

Preferably, the base composition is premanufactured, i.e., prepared at a location remote from where the mixing step is performed or prepared in large quantities. The term "large quantities" is herein defined as a quantity greater than that needed to produce a single final product and is preferably many multiples times that. The base composition is typically premanufactured in large batches. The base composition may be prepared by methods known in the art.

Rheology Modifying Agents

Suitable rheology modifying agents include, but are not limited to, hydroxypropyl distarch phosphate, carbomer, guar hydroxypropyltrimonium chloride, hydroxypropyl guar, sodium hydroxypropyl starch phosphate, sodium hyaluronate, carboxymethyl cellulose, dermatan sulphate, chondrotin sulphate, hydroxypropyl methylcellulose, pectin, xanthan gum, sclerotium gum, and any combination of any of the foregoing. Preferably, the base composition contains at least two different rheology modifying agents. Preferred combinations of rheology modifying agents include, but are not limited to, hydroxypropyl distarch phosphate and carbomer; guar hydroxypropyltrimonium chloride and hydroxypropyl guar; sodium hydroxypropyl starch phosphate and carbomer; and hydroxypropyl methylcellulose and pectin.

Generally, the formulation contains from about 0.01 to about 35% by weight, preferably from about 0.4 to about 10% by weight, and more preferably from about 0.4 to about 6% by weight of rheology modifying agent, based upon 100% weight of total formulation. One or more rheology modifying agents may be included in the formulation besides those included in the base composition.

Hydrophobic Active Agent or Hydrophobic Adjuvant Dispersion

The dispersion is generally a homogenous fluid which is stable for a commercially relevant period of time. The dispersion typically remains stable for at least 2 weeks and preferably at least 2 months.

A hydrophobic active agent or hydrophobic adjuvant is an active agent or adjuvant which has a non polar property which makes it essentially insoluble in water or water and polar solvent solution. Hydrophobic active agents and hydrophobic adjuvants of the present invention include, but are not limited to, partially and fully hydrophobic active agents and partially and fully hydrophobic adjuvants. For example, hydrophobic active agents encompassed by the present invention include compounds and complexes which contain a hydrophobic moiety.

The formulation of the present invention may also include non-hydrophobic active agents and non-hydrophobic adjuvants.

The dispersion containing the suspended particles generally contains from about 0.01 to about 70% by weight of oil, based upon 100% weight of total dispersion. Preferably, the dispersion contains from about 1.0 to about 50% by weight of oil, based upon 100% weight of total dispersion. The oil component of the formulation may include active agents and adjuvants which are oils.

The dispersion is a suspension of liquid or solid particles of colloidal size or larger in a liquid medium. Generally, the dispersion contains suspended particles, such as oil particles (or oil droplets), having a diameter less than about 500 nm. The diameter of the suspended particles preferably ranges from about 50 nm to about 500 nm and more preferably from about 250 to about 500 nm. Preferably, the oil droplets contain one or more lipophilic materials. The oil droplets may have a charge as determined by zeta potential measurements. The oil droplets may be prepared by ultra high shear mixing or microfluidization. Preferred oil containing dispersions are sold under the tradename Sansurf™ by Collaborative Laboratories, Inc. of East Setauket, N.Y., and Dermasomes™ by Microfluidics Corp. of Newton, Mass.

According to a preferred embodiment, the dispersion is prepared by mixing from about 0.1% to about 70% by weight of hydrophobic active agent and/or hydrophobic adjuvant with from about 30% to about 99.9% by weighs of aqueous phase under high pressure and high shear conditions, based upon 100% weight of total dispersion. The aqueous phase contains water and, optionally, other hydrophilic adjuvants. More preferably, the mixing is performed with shearing at a pressure of from about 9,000 to about 25,000 psi to form a dispersion having an average particle size ranging from about 50 to about 500 nm.

Active Agents

Suitable active agents include, but are not limited to, anti-acne agents, antimicrobial agents, antiinflammatory agents, analgesics, antietythemal agents, antipruritic agents, antiedemal agents, antipsoriatic agents, antifungal agents, skin protectants, sunscreen agents, vitamins, antioxidants, scavengers, antiirritants, antibacterial agents, antiviral agents, antiaging agents, protoprotection agents, hair growth enhancers, hair growth inhibitors, hair removal agents, antidandruff agents, anti-seborrheic agents, exfoliating agents, wound healing agents, anti-ectoparacitic agents, sebum modulators, immunomodulators, hormones, botanicals, moisturizers, astringents, cleansers, sensates, antibiotics, anesthetics, steroids, tissue healing substances, tissue regenerating substances, amino acids, peptides, minerals, ceramides, biohyaluronic acids, and any combination of any of the foregoing.

Preferred anti-acne agents include, but are not limited to, salicylic acid, retinoic acid, alpha hydroxy acid, benzyl peroxide, sodium sulfacetamide, clindamycin, and any combination of any of the foregoing. Preferred combinations of anti-acne agents to be incorporated in the formulation include salicylic acid, retinoic acid, and hydrocortisone; sodium sulfacetamide and clindamycin; salicylic acid and clindamycin; and salicylic acid, alpha hydroxy acid, and tetrahydrozoline.

Suitable antimicrobial agents include, but are not limited to, benzalkonium chloride, benzethonium chloride, chlorhexidine gluconate, chloroxylenol, cloflucarban, fluorosalan, hexachlorophene, hexylresorcinol, iodine complex, iodine tincture, para-chloromercuriphenol, phenylmercuric nitrate, thimerosal, vitromersol, zyloxin, triclocarban, triclosan, methyl-benzethonium chloride, nonyl phenoxypoly(ethyleneoxy) ethanol-iodine, para-chloro-meta-xylenol, providone-iodine complex, poloxamer-iodine complex, triclocarban, undecoylium chloride-iodine complex, and any combination of any of the foregoing.

Suitable antiinflammatory agents include, but are not limited to, alidoxa, allantoin, aloe vera, aluminum acetate, aluminum hydroxide, bismuth subnitrate, boric acid, calamine, casein, cellulose, microporous, cholecatciferol, cocoa butter, cod liver oil, colloidal oatmeal, cystein hydrochloride, dexpanthenol, dimethicone, glycerin, kaolin, lanolin, live yeast cell derivative, mineral oil, peruvian balsam, petrolatum, protein hydrolysate, racemethionine, shark liver oil, sodium bicarbonate, sulfur, talc, tannic acid, topical starch, vitamin A, vitamin E, white petrolatum, zinc acetate, zinc carbonate, zinc oxide, hydrocortisone, betamethasone, ibuprofen, indomethicin, acetyl salicylic acid, tacrolimus, flucoinolone acetonide, sodium sulfacetamide, and any combination of any of the foregoing.

Suitable analgesics include, but are not limited to, diphenhydramine, tripeiennamine, benzocaine, dibucaine, lidocaine, tetracaine, camphor, menthol, phenol, resorcinol, matacresol, juniper tar, methylsalicylate, turpentine oil, capsicum, methyl nicotinate, b-glucan, and any combination of any of the foregoing.

Suitable antietythermal agents include, but is not limited to, tetrahydrozoline and hydracortisone.

Suitable antipruritic agents include, but are not limited to, benadryl, pramoxine, antihistamines, and any combination of any of the foregoing.

Suitable antiedemal agents, include, but are not limited to, pregnenalone acetate, tanin glyrosides, and any combination of any of the foregoing.

Suitable antipsoriatic agents include, but are not limited to, caleipotriene, coal tar, anthralin, vitamin A, and any combination of any of the foregoing. Preferred combinations of antipsoriatic agents include, but are not limited to, hydrocortisone, retinoic acid, and alpha hydroxy acid; dovonex, salicylic acid, and a sunscreen agent; indomethicin, salicylic acid, and urea; anthralin and salicylic acid; and anthralin and indomethicin. Other suitable antipsoriatic agents include, but are not limited to, caleipotriene, coal tar, anthralin, vitamin A, and any combination of any of the foregoing.

Suitable antifungal agents include, but are not limited to, clioquinol, haloprogin, miconazole nitrate, clotrimazole, metronidazole, toinaftate, undecylenic acid, iodoquinol, and any combination of any of the foregoing.

Suitable skin protectants include, but are not limited to, cocoa butter, dimethicone, petrolatum, white petrolatum, glycerin, shark liver oil, allantoin, and any combination of any of the foregoing.

Suitable sunscreen agents include, but are not limited to, ethylhexyl methoxycinnamate, avobenzone, benzophenone-3, octacrylene, titanium dioxide, zinc oxide, and any combination of any of the foregoing.

Suitable antioxidants include, but are not limited to, scavengers for lipid free radicals and peroxyl radicals, quenching agents, and any combination of any of the foregoing. Suitable antioxidants include, but are not limited to, tocopherol, BHT, beta carotene, vitamin A, ascorbic acid, ubiquinol, ferulic acid, azelaic acid, thymol, catechin, sinapic acid, EDTA, lactoferrin, rosmariquinone, hydroxytyrosole, sesamol, 2-thioxanthine, nausin, malvin, carvacone, chalcones, glutathione isopropyl ester, xanthine, melanin, guanisone, lophorphyrins, 8-hydroxyxanthine, 2-thioxanthione, vitamin $B_{12}$, plant alkaloids, catalase, quercetin, tyrosine, SOD, cysteine, methionine, genistein, NDG, procyanidin, hamamelitannin, ubiquinone, trolox, licorice extract, propyl gallate, sinapic acid, and any combination of any of the foregoing. Suitable vitamins include, but are not limited to, vitamin E, vitamin A palmitate, vitamin D, vitamin F, vitamin $B_6$, vitamin $B_3$, vitamin $B_{12}$, vitamin C, ascorbyl palmitate, vitamin E acetate, biotin, niacin, DL-panthenol, and any combination of any of the foregoing.

A preferred sunscreen agent is a mixture of ethylhexyl methoxycinnamate, butyl methoxydibenzoylmethane, cyclomethicone, phospholipids, and water, and is available as Solarease™ from Collaborative Laboratories, Inc. of East Setauket, N.Y.

Suitable amino acids include, but are not limited to, glycine, serine, and any combination of any of the foregoing.

Aesthetic Modifying Agents

The formulation preferably includes at least one aesthetic modifying agent. An aesthetic modifying agent is a material which imparts desirable tactile, olfactory, taste or visual properties to the surface to which the formulation is applied. The aesthetic modifying agent may be hydrophobic or hydrophilic. The aesthetic modifying agent is preferably hydrophobic and is more preferably an oil, wax, solid or paste.

A dispersion of one or more hydrophobic aesthetic modifying agents is preferably prepared before the hydrophobic aesthetic modifying agents are incorporated into the formulation. The hydrophobic aesthetic modifying agents may be dispersed into an aqueous phase by methods known in the art, such as by ultra high shear mixing and microfluidization.

The final formulation may be prepared by mixing the dispersions containing the hydrophobic aesthetic modifying agents with the base composition and any other additives. Since the hydrophobic aesthetic modifying agents are added to the base composition as dispersions, heating and other expensive processing steps are not required to obtain a homogenous final formulation.

An example of an aesthetic modifying agent is a mono, di, tri or poly alkyl ester or ether of a di, tri, or polyhydroxy compound, such as ethylene glycol, propylene glycol, glycerin, sorbitol or other polyol compound. Examples of such esters and ethers include, but are not limited to, saturated and unsaturated, linear and branched vegetable oils, such as soybean oil, babassu oil, castor oil, cottonseed oil, chinese tallow oil, crambe oil, perilla oil, danish rapeseed oil, rice bran oil, palm oil, palm kernel oil, olive oil, linseed oil, coconut oil, sunflower oil, safflower oil, peanut oil and corn oil Preferred saturated and unsaturated vegetable oils are those having fatty acid components with 6 to 24 carbon atoms. A more preferred vegetable oil is soybean oil.

An example of a hydrophobic aesthetic modifying agent is a compound having the formula $C_nH_{(2n+2-m)}$ where n is an integer greater than or equal to 6 and m is 0 or an even integer no greater than n Such compounds include, but are not limited to, saturated and unsaturated, linear, branched, and cyclic hydrocarbon chains. Preferred examples of such compounds include, but are not limited, mineral oil, petrolatum, permethyl fluids, polybutylenes, and polyisobutylenes.

Another example of a hydrophobic aesthetic modifying agent has the formula

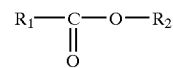

or the formula:

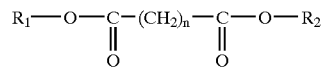

where $R_1$ is a saturated or unsaturated, linear, branched or cyclic $C_1$–$C_{24}$ alkyl; $R_2$ is hydrogen or a saturated or unsaturated, liner, branched or cyclic $C_1$–$C_{24}$ alkyl; and n is an integer from 0 to 20. Examples of such aesthetic modifying agents include, but are not limited to, isopropyl palmitate and diisopropyl adipate.

Yet another aesthetic modifying agent is silicone. Silicone may provide lubrication and/or shine to the formulation. Preferably, the silicone is insoluble in water. Suitable water-insoluble silicone materials include, but are not limited to, polyalkylsiloxanes, polyarylsiloxanes, polyalkylarylsiloxanes, polysiloxane gums and polyethersiloxane copolymers. Examples of suitable silicone materials are disclosed in U.S. Pat. Nos. 4,788,006; 4,341,799; 4,152,416; 3,964,500; 3,208,911; 4,364,837 and 4,465,619, all of which are incorporated herein by reference.

Another suitable hydrophobic material which can be suspended in the formulation has the formula

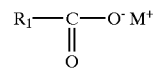

where $R_1$ is a saturated or unsaturated, linear, branched or cyclic alkyl having 2 to 24 carbon atoms; $M^{(+)}$ is $N^+R_2R_3R_4R_5$; $R_2$, $R_3$ and $R_4$ are hydrogen or a saturated or unsaturated, linear or branched alkyl or hydroxyalkyl having from 1 to 10 carbon atoms; and $R_5$ is a saturated or unsaturated, linear, branched or cyclic alkyl or substituted alkyl having 2 to 24 carbon atoms. An example of such a material is lauramine oleate.

Other Adjuvants

Other suitable adjuvants which may be included in the formulation include, but are not limited to, pH adjusters, emollients, conditioning agents, chelating agents, gelling agents, viscosifiers, colorants, fragrances, odor masking agents, UV stabilizer, preservatives, and any combination of any of the foregoing. Preferred pH adjusters include, but are not limited to, aminomethyl propanol, aminomethylpropane diol, triethanolamine, citric acid, sodium hydroxide, acetic acid, potassium hydroxide, lactic acid, and any combination of any of the foregoing.

Suitable conditioning agents include, but are not limited to, cyclomethicone, petrolatum, dimethicone, dimethiconol, silicone, quaternary amines, and any combination of any of the foregoing.

The formulation preferably contains less than about 0.5% by weight of preservatives, based upon 100% weight of total formulation. More preferably, the formulation contains from about 0.25 to about 0.5% by weight of preservatives, based upon 100% weight of total formulation.

While the invention has been particularly shown and described with reference to preferred embodiments thereof, it will be understood by those skilled in the art that various changes in form and details may be made therein without departing from the spirit and scope of the invention.

What is claimed is:

1. A method for producing a customized cosmetic or pharmaceutical product comprising the steps of:

formulating a set of structured questions:

querying a user based on said questions to obtain the user's age, sex, race, skin type, skin color, allergies, season, geographical location, and anatomical location of application of the customized cosmetic or pharmaceutical product to produce a user profile;

requesting, by a user, at least one of a specific product and a product compound;

generating a basic formulation based on the user's request;

altering the basic formulation based on the user's profile to create a customized formulation; and outputting the customized formulation for subsequent manufacture of the customized product.

2. The method of claim 1, further comprising the step of further modifying the initial formulation in accordance with external factors.

3. The method of claim 1, wherein the outputting step comprises sending the customized formulation to a manufacturing facility.

4. The method of claim 1, wherein the outputting step comprises printing the customized formulation.

5. The method of claim 4, wherein the formulation is printed as a prescription.

6. The method of claim 1, wherein the outputting step comprises electronically sending the customized formulation to a manufacturing facility.

7. The method of claim 1, wherein the outputting step comprises outputting the customized formulation for subsequent manufacture of the customized product to a manufacturing facility located remotely from the user.

* * * * *